United States Patent
Riggs et al.

(10) Patent No.: US 8,748,347 B2
(45) Date of Patent: *Jun. 10, 2014

(54) METHOD FOR COMBATING HARMFUL FUNGI

(75) Inventors: Richard Riggs, Mannheim (DE); Dieter Strobel, Herxheim am Berg (DE); Jochen Prochnow, Neustadt (DE); Helmut Herrmann, Rottenburg (DE); Michael Ishaque, Mannheim (DE); Christian Bittner, Bensheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/260,796

(22) PCT Filed: Mar. 25, 2010

(86) PCT No.: PCT/EP2010/053897
§ 371 (c)(1),
(2), (4) Date: Dec. 13, 2011

(87) PCT Pub. No.: WO2010/115720
PCT Pub. Date: Oct. 14, 2010

(65) Prior Publication Data
US 2012/0083497 A1    Apr. 5, 2012

(30) Foreign Application Priority Data
Apr. 2, 2009 (EP) .................... 09157172

(51) Int. Cl.
*A01N 43/00* (2006.01)
*A61K 31/535* (2006.01)
*A61K 31/24* (2006.01)

(52) U.S. Cl.
USPC ........ 504/139; 504/117; 514/239.5; 514/383; 514/521; 514/535; 514/537

(58) Field of Classification Search
USPC .............. 504/116.1, 117, 118, 129, 138, 139; 424/405; 514/239.5
See application file for complete search history.

(56) References Cited

U.S. PATENT DOCUMENTS

| 5,374,639 | A | 12/1994 | Sutter et al. | |
| 8,404,263 | B2* | 3/2013 | Ishaque et al. | 424/405 |
| 2012/0017503 | A1* | 1/2012 | Riggs et al. | 47/57.7 |

FOREIGN PATENT DOCUMENTS

| CA | 1 195 246 | 10/1985 |
| EP | 0 083 308 | 7/1983 |
| EP | 0 549 532 | 6/1993 |
| JP | 57 182271 | 11/1982 |
| WO | WO 2008/085682 | 7/2008 |

OTHER PUBLICATIONS

Berestetskiy, A.O., "A Review of Fungal Phytotoxins: from Basic Studies to Practical Use", Applied Biochemistry and Microbiology, 2008, p. 453-465, vol. 44, No. 5.
Heiser, Ingrid, et al. "Photodynamic oxygen activation by rubellin D, a phytotoxin produced by *Ramularia coll-cygni* (Sutton et Waller)", Physiological and Molecular Plant Pathology, 2003, p. 29-36, vol. 62.
Heiser, Ingrid, et al. "The formation of reactive oxygen species by fungal and bacterial phytotoxins", Plant Physiol. Biochem., 1998, p. 703-713, vol. 36, No. 10.
Miethbauer, Sebastian, et al. "Uredinorubellins and Caeruleoramularin, Photodynamically active anthraquinone derivatives produced by Two species of the genus *Ramularia*", J. Nat. prod., 2008, p. 1371-1375, vol. 71.
Miethbauer, S. et al., "The phytopathogenic Fungus *Ramularia collcygni* Produces Biologically Active Rubellins on Infected Barley Leaves", J. Phytopathology, 2003, p. 665-668, vol. 151.
Youngman, Richard J., et al. "Photodynamic and Reductive mechanisms of oxygen activation by the fingal phytotoxins, cerosporin and dothistromin" Oxygen Radicals in Chemistry and Biology, Walter de Gruyter, Berlin, 198 New York 1984, p. 501-505.
Youngman, Richard J. et al. "The phytodynamic generation of single molecular oxygen by the fungal phytotoxin, cercosporin", Photobiochemistry and photobiophysics, 1983, p. 109-119, vol. 6.
International Search Report prepared in International Application No. PCT/EP2010/053897, filed Mar. 25, 2010.
International Preliminary Report on Patentability from corresponding International Application No. PCT/EP2010/053897, filed Mar. 25, 2010.
Database WPI, Thomson Scientific, (1982), XP002629583, JP 57 182371.
Gabriele, P. et al., "Protection of Mildewcides and Fungicides From Ultraviolet Light Induced Photo-oxidation", Journal of Coatings Technology, (1984), pp. 33-48, vol. 56, No. 712.
Lu, J. et al., "$TiO_2$ photocatalytic antifungal technique for crops diseases control", Journal of Environmental Sciences, (2006), pp. 397-401, vol. 18, No. 2.
Miethbauer, S. et al., "Biosynthesis of photodynamically active rubellins and structure elucidation of new anthraquinone derivatives produced by *Ramularia collo-cygni*", Phytochemistry, (2006), pp. 1206-1213, vol. 67, No. 12.
Tawata, S. et al., "Synthesis and Antifungal Activity of Cinnamic Acid Esters", Bioscience Biotechnology Biochemistry, (1996), pp. 909-910, vol. 60, No. 5.

* cited by examiner

*Primary Examiner* — My-Chau T Tran
(74) *Attorney, Agent, or Firm* — Brinks Gilson & Lione

(57) ABSTRACT

The present invention relates to methods, use and compositions for combating harmful fungi and bacteria in plants. More specifically, it relates to methods and compositions for controlling, preventing, or treating plant pathogens using UV filters for combating phytotoxin-producing fungi and/or bacteria, in particular, for combating harmful fungi and/or bacteria producing photodynamically active phytotoxins.

29 Claims, No Drawings

METHOD FOR COMBATING HARMFUL FUNGI

This application is a National Stage application of International Application No. PCT/EP2010/053897 filed Mar. 25, 2010, the entire contents of which is hereby incorporated herein by reference. This application also claims priority under 35 U.S.C. §119 to European Patent Application No. 09157172.9, filed Apr. 2, 2009, the entire contents of which is hereby incorporated herein by reference.

The present invention relates to methods, use and compositions for combating harmful fungi and bacteria in plants. More specifically, it relates to methods and compositions for controlling, preventing, or treating plant pathogens using UV filters for combating phytotoxin-producing fungi and/or bacteria, in particular, for combating harmful fungi and/or bacteria producing photodynamically active phytotoxins.

Farmers typically rely on genetic resistance to provide protection from plant pathogen infection and disease. However, sufficient genetic resistance is not always available in the crops being produced or undesirable traits are linked to the genetic resistance genetic loci. Farmers must then apply pesticides to control the pathogen infections, significantly increasing the cost of growing the crops and impact to the environment.

One typical problem arising in the field of pest control lies in the need to reduce the dosage rates of the pesticides in order to reduce or avoid unfavorable environmental or toxicological effects whilst still allowing pathogen control. Another problem encountered concerns the need to have available fungal and/or bacterial pathogen control agents which show an improved action against harmful fungi and/or bacteria with a reduced amount of active compounds applied and/or a broadened spectrum of pathogens controlled.

Another difficulty in relation to the use of pesticides is that the repeated and exclusive application of an individual pesticidal compound or compounds of the same mode of action or chemical class leads in many cases to a rapid selection of bacterial or fungal pathogens that have developed natural or adapted resistance against the active compound or chemical class in question.

Another problem underlying the present invention is the desire to reduce the development of disease symptoms caused by harmful fungi and bacteria. Many disease symptoms are caused by the action of phytotoxin produced by harmful fungi. The effects of such phytotoxins on plants is characterized by the appearance of disease symptoms, such as wilting, general growth suppression, chloroses, necroses, and spotting of the areal parts (Berestetsky 2008, Appl. Biochem. Microbiol. 44(5), 453-465). Many, if not all of these disease symptoms are light-dependent and involve, for example, the light-dependent formation of phytotoxic reactive oxygen species such as singlet oxygen or superoxide (Heiser et al. 1998, Plant Physiol. Biochem. 36(10), 703-13).

Thus, a further problem encountered is the reduction of light-dependent disease symptoms caused by harmful fungi and bacteria. Light-dependent plant damage is, for example, caused by photodynamically active phytotoxins such as rubellins, uredorubellins, caeruleoramularin, cercosporin, dothistromin, naphthazarin toxins (e.g. dihydrofusarubin, isomarticin), tentoxins, tabtoxins and cebetins (Miethbauer et al. 2008, J. nat. Prod. 71, 1371-75; Miethbauer et al. 2006, Phytochem. 67, 1206-13; Miethbauer et al. 2003, J. Phytopathol. 151, 665-68; Heiser et al. 2003, Physiol. Mol. Plant Pathol. 62, 29-36; Heiser et al. 1998, Plant Physiol. Biochem. 36(10), 703-13; Youngman and Elstner 1984, In Oxygen radicals in Chemistry and Biology, Walter der Gruyter, Berlin, 501-505; Youngman et al. 1983, Photobiochem. Photobiophys. 6, 109-119). Such phytotoxins are produced by a wide number of fungal and bacterial genera, only some of which have been identified yet: e.g. *Ramularia, Cercospora, Dothistroma, Mycosphaerella, Fusarium, Alternaria, Aspergillus, Penicillium, Sclerotinia, Septoria, Pseudomonas* (Berestetsky 2008, Appl. Biochem. Microbiol. 44(5), 453-465; Heiser et al. 1998, Plant Physiol. Biochem. 36(10), 703-13).

It was therefore an object of the present invention to provide uses and methods which solve the problems outlined above. This object is in part or in whole achieved by the uses, methods and compositions defined below.

Accordingly, the present invention relates to the use of at least one UV filter chosen from the following groups:

A) benzotriazoles, such as 2-(2H-benzotriazol-2-yl)-4,6-bis(1-methyl-1-phenylethyl)phenol (Tinuvin® 900, CIBA AG), [3-[3-(2H-benzotriazol-2-yl)-5-(1,1-dimethylethyl)-4-hydroxyphenyl]-1-oxopropyl]-w-[3-[3-(2H benzotriazol-2-yl)-5-(1,1-dimethylethyl)-4-hydroxyphenyl]-1-oxopropoxy]poly(oxy-1,2-ethanediyl) (Tinuvin® 1130, CIBA AG), 6-tert-butyl-2-(5-chloro-2H-benzotriazol-2-yl)-4-methylphenol, 2,4-ditert-butyl-6-(5-chloro-2H-benzotriazol-2-yl)-phenol, 2-(2H-benzotriazol-2-yl)-4,6-di-tert-pentylphenol, 2-(2H-benzotriazol-2-yl)-4-(1,1,3,3-tetramethylbutyl)-phenol, 2-(2H-benzotriazol-2-yl)-4-methylphenol, 2-(2H-benzotriazol-2-yl)-4,6-bis(1-methyl-1-phenylethyl)phenol, compounds of formula I

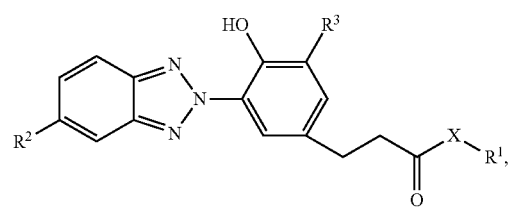

wherein
X is NH or O;
$R^1$ is $[C_2\text{-}C_4\text{-alkoxy}]_n\text{-}(C_1\text{-}C_{18}\text{-alkyl})$ or $-[CH_2CH_2NH]_n-H$;
$R^2$ is H or Cl;
$R^3$ is H or $C_1\text{-}C_8$-alkyl; and
n is an integer between 3 and 50;

B) Cyanoacrylate derivatives, such as ethyl 2-cyano-3-phenylcinnamate (Uvinul® 3035, BASF SE), 2-cyano-3,3-diphenylacrylic acid-2'-ethylhexyl ester or 2-ethylhexyl-2-cyano-3-phenylcinnamate (octocrylene, Uvinul® 539 T, Uvinul 3039, BASF SE), compounds of formula

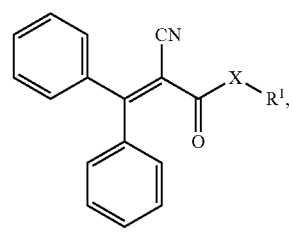

wherein
X is NH or O;
$R^1$ is $[C_2\text{-}C_4\text{-alkoxy}]_n\text{-}(C_1\text{-}C_{18}\text{-alkyl})$ or $-[CH_2CH_2NH]_n-H$;
$R^2$ is H or Cl; and
n is an integer between 3 and 50;

C) para-aminobenzoic acid (PABA) derivatives, especially esters, such as ethyl-PABA, ethoxylated PABA, ethyldihydroxypropyl-PABA, Glycerol-PABA, 2-ethylhexyl 4-(dimethylamino)benzoate (Uvinul® MC 80), 2-octyl 4-(dimethylamino)benzoate, amyl 4-(dimethylamino) benzoate, 4-bis(polyethoxy) 4-amino benzoic acid polyethoxyethyl ester (Uvinul® P 25, BASF SE);

D) esters of salicylic acid, such as 2-ethylhexyl salicylate, 4-isopropylbenzyl salicylate, homomethyl salicylate, TEA salicylate (Neo Heliopan® TS, Haarmann and Reimer), dipropyleneglycol salicylate;

E) esters of cinnamic acid, such as 2-ethylhexyl 4-methoxycinnamate (Uvinul® MC 80), octyl-p-methoxycinnamate, propyl 4-methoxycinnamate, isoamyl 4-methoxycinnamate, conoxate, diisopropyl methylcinnamate, etocrylene (Uvinul® N 35, BASF SE), compounds of furthermore compounds of formula

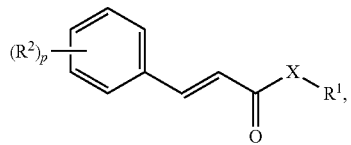

wherein
X is NH or O;
$R^1$ is H or $[C_2-C_4\text{-alkoxy}]_n\text{-}(C_1-C_{18}\text{-alkyl})$ or $-[CH_2CH_2NH]_n-H$;
$R^2$ is OH or $C_1-C_8$-alkoxy;
p is an integer between 0 and 5; and
n is an integer between 3 and 50;

F) derivatives of benzophenone, such as 2-hydroxy-4-methoxybenzophenone (Uvinul® M 40, BASF SE), 2-hydroxy-4-methoxy-4'-methylbenzophenone, 2,2'-dihydroxy-4-methoxybenzophenone, 2-(4-diethylamino-2-hydroxybenzoyl)benzoic acid hexylester (Uvinul® A Plus, BASF SE), 4-n-octyloxy-2-hydroxybenzophenone (Uvinul® 3008, BASF SE), 2-hydroxybenzophenone derivatives such as 4-hydroxy-, 4-methoxy-, 4-octyloxy-, 4-decyloxy-, 4-dodecyloxy-, 4-benzyloxy-, 4,2',4'-trihydroxy-, 2'-hydroxy-4,4'-dimethoxy-2-hydroxybenzophenone), compounds of formula:

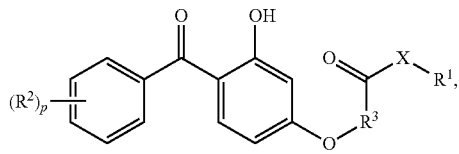

wherein
X is NH or O;
$R^1$ is H or $[C_2-C_4\text{-alkoxy}]_n\text{-}(C_1-C_{18}\text{-alkyl})$ or $-[CH_2CH_2NH]_n-H$;
$R^2$ is OH or $C_1-C_8$-alkoxy;
p is an integer between 0 and 5; and
$R^3$ is H or $C_1-C_8$-alkyl; and
n is an integer between 3 and 50;

G) sulfonic acid derivatives of benzophenones, such as 2-hydroxy-4-methoxybenzophenone-5-sulfonic acid (Uvinul® MS 40, BASF SE) and its salts, 2,2'-dihydroxy-4,4'-dimethoxybenzophenone-5,5'-sulfonic acid and its salts (disodium salt: Uvinul® DS 49, BASF SE);

H) 3-benzylidenecamphor and derivatives thereof, such as 3-(4'-methylbenzylidene)d-1-camphor, benzylidiene camphor sulfonic acid (Mexoryl® SO, Chimex);

I) sulfonic acid derivatives of 3-benzylidenecamphor, such as 4-(2-oxo-3-bornylidenemethyl)benzenesulfonic acid and 2-methyl-5-(2-oxo-3-bornylidene)sulfonic acid and salts thereof;

J) esters of benzalmalonic acid, such as 2-ethylhexyl 4-methoxybenzmalonate;

K) triazine derivatives, such as dioctylbutamidotriazone (Uvasorb® HEB, Sigma), 2,4,6-trinanilino-p-(carbo-2'-ethyl-hexyl-1'-oxy)-1,3,5-triazine (Uvinul® T 150, BASF SE), 2-[4-[(2-Hydroxy-3-(2'-ethyl)hexyl)oxy]-2-hydroxyphenyl]-4,6bis(2,4-dimethylphenyl)-1,3,5-triazine (Tinuvin® 405, CIBA AG), anisotriazine (Tinosorb® S, CIBA AG), 2,4,6-tris(diisobutyl 4'-aminobenzalmalonate)-s-triazine, compounds of formula:

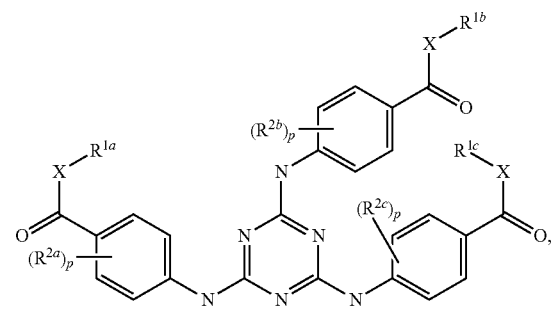

wherein
X is NH or O;
$R^{1a}, R^{1b}, R^{1c}$ are independently of each other H, $[C_2-C_4\text{-alkoxy}]_n\text{-}(C_1-C_{18}\text{-alkyl})$ or $-[CH_2CH_2NH]_n-H$;
$R^{2a}, R^{2b}, R^{2c}$ are independently of each other OH or $C_1-C_8$-alkoxy;
p is an integer between 0 and 4; and
n is an integer between 3 and 50;

L) Propane-1,3-diones, such as, 1-(4-tert-butylphenyl)-3-(4'-methoxyphenyl)propane-1,3-dione;

M) 2-phenylbenzimidazole-5-sulfonic acid or 2-phenylbenzimidazole-4-sulfonic acid and alkali metal, alkaline earth metal, ammonium, alkylammonium, alkanolammonium and glucammonium salts thereof;

N) derivatives of benzoylmethane, such as, 1-(4'-tert-butylphenyl)-3-(4'-methoxyphenyl)propane-1,3-dione, 4-tert-butyl-4'-methoxydibenzoylmethane or 1-phenyl-3-(4'-isopropylphenyl)propane-1,3-dione;

O) Aminohydroxy-substituted derivatives of benzophenones, such as N,N-diethylaminohydroxybenzoyl-n-hexylbenzoate; and P) inorganic absorbers e.g. based on ZnO (e.g. Z-Cote® products, BASF SE), $TiO_2$ (e.g. T-Lite™ products, BASF SE) or $CeO_2$; and Q) mixtures of UV filters of groups A) to O), such as a mixture of p-methoxycinnamic acid ethylhexyl ester (65%) and 2-(4-diethylamino-2-hydroxybenzoyl)benzoic acid hexylester (35%) (Uvinul® A Plus B, BASF SE);

for combating harmful fungi and/or bacteria in plants.

The UV filters of groups A) to Q) are known and are used in cosmetics, such as sunscreen, lipsticks or for stabilization of polymers such as plastics. Many of them are commercially available (such as Uvinul® products (BASF SE) or Tinuvin® products (CIBA AG)) or may be found in patent applications such as EP 0 280 650; U.S. 61/160,124. UV filters encompass compounds of the following classes: benzophenones, benzotriazoles, cyanoacrylates, cinnamic acid esters, para-aminobenzoates (PABA), naphthalimides, hydroxyphenyltriazines, oxalanilides or metal oxides. Such compounds EP 0 280 650 discloses benzotriazoles of formula

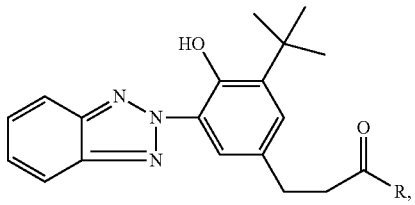

wherein R is e.g. —OCH$_2$CH$_2$OCH$_2$CH$_2$OC$_2$H$_5$ or —NHCH$_2$CH$_2$OC$_2$H$_5$.

Tinuvin® 384-2: a commercially available UV filter (CIBA AG) from the class of benzotriazoles (95% benzenepropionic acid, 3-(2H-benzotriazol-2-yl)-5-(1,1-dimethylethyl)-4-hydroxy-, C$_{7-9}$-alkyl ester and 5% 1-methoxy-2-propylacetate).

Tinuvin® 109: a commercially available UV filter (CIBA AG) from the class of benzotriazoles (mixture of 45-55% (w/w) of 3-(5-chloro-2H-benzotriazol-2-yl)-5-(1,1-dimethylethyl)-4-hydroxy-phenylpropionic acid octylester and 45-55% (w/w) 3-(5-chloro-2H-benzotriazol-2-yl)-5-(1,1-dimethylethyl)-4-hydroxy-phenylpropionic acid octylester-2-ethylhexylester.

Tinuvin® 1130: a commercially available UV filter (CIBA AG) from the class of benzotriazoles [3-[3-(2H-benzotriazol-2-yl)-5-(1,1-dimethylethyl)-4-hydroxyphenyl]-1-oxopropyl]-w-[3-[3-(2Hbenzotriazol-2-yl)-5-(1,1-dimethylethyl)-4-hydroxyphenyl]-1-oxopropoxy]poly(oxy-1,2-ethanediyl) of the formula

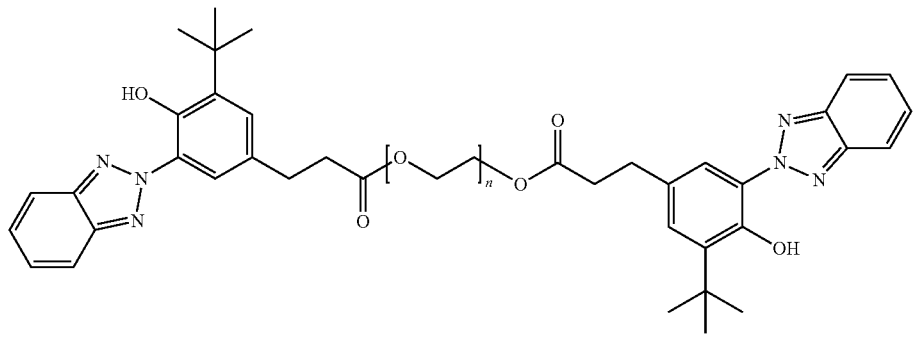

n = 6-7

Uvinul® P25: a commercially available UV filter (BASF SE) p-aminobenzoic acid ethoxylate (45) (mol. wt. Ca. 1,265 g/mol)

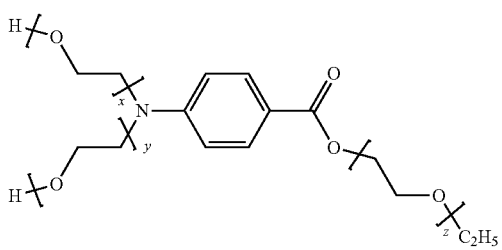

Uvinul®P25

Tinuvin® 99, Tinuvin® 384-2: commercially available UV filters (CAS-No. 127519-17-9; CIBA AG) of formula

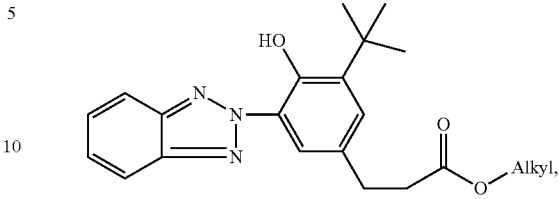

wherein alkyl means a mixture of straight-chain and/or branched C$_7$-C$_9$-alkyl groups.

Tinuvin® R 796: a commercially available UV filter (CIBA AG) from the class of benzotriazoles (CAS-No. 96478-09-0):

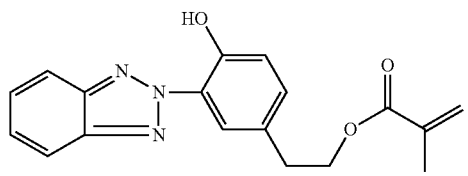 [SMILES: C=C(C)C(=O)OCCc1ccc(O)c(-n2nc3ccccc3n2)c1]

Tinuvin® R 796.

Further suitable UV-Absorber are to be found in the document "Cosmetic Legislation", Vol. 1, Cosmetic Products, European Commission 1999, 64-66, which is referred to herewith. Suitable UV filters are also found in lines 14 to 30 ([0030]) on page 6 of the document EP 1 191 041 A2, which is also referred to herewith and forms part of the disclosure of the present inventions.

Further examples for suitable UV filters are:
  belonging to class A) of benzotriazoles or 2-(2'-Hydroxyphenyl)benzotriazoles, such as 2-(2H-benzotriazole-2-yl)-4-methyl-6-(2-methyl-3-((1,1,3,3-tetramethyl-1-(trimethylsilyloxy)disiloxanyl)-propyl)phenol, 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-[2'-hydroxy-5-(1,1,3,3-tetramethylbutyl)phenyl]benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'- octyloxyphenyl)benzotriazole, 2-(3',5'-di-tert-amyl-2'-hydroxyphenyl)benzotriazole, 2-[3',5'-bis(α,α-dimethylbenzyl)-2'-hydroxyphenyl]benzotriazole, 2-[3'-tert-butyl-2'-hydroxy-5'-(2-octyloxycarbonylethyl)phenyl]-5-chlorobenzotriazole, 2-[3'-tert-butyl-5'-(2-(2-ethylhexyloxy)-carbonylethyl)-2'-hydroxyphenyl]-5-chlorobenzotriazole, 2[3'-tert-butyl-2'-hydroxy-5'-(2-methoxycarbonylethyl)phenyl]-5-chlorobenzotriazole, 2-[3'-tert-butyl-2'-hydroxy-5'-(2-methoxycarbonylethyl)phenyl]benzotriazole, 2-[3'-tert-butyl-2'-hydroxy-5'-(2-octyloxycarbonylethyl)phenyl]-benzotriazole, 2-[3'-tert-butyl-5'-(2-(2-ethylhexyloxy)carbonylethyl)-2'-hydroxyphenyl]-benzotriazole, 2-(3'-dodecyl-2'-hydroxy-5'-methylphenyl)benzotriazole, 2-[3'-tert-butyl-2'-hydroxy-5'-(2-isooctyloxycarbonylethyl)phenyl]benzotriazole, 2,2'-methylenbis[4-(1,1,3,3-tetramethylbutyl)-6-benzotriazol-2-yl-phenol], esterified product of 2-[3'-tert-butyl-5'-(2-methoxycarbonylethyl)-2'-hydroxyphenyl]-2H-benzotriazole and polyethylenglycol 300, [R—CH$_2$CH$_2$—COO (CH$_2$)$_3$—]$_2$ with R being 3'-tert-butyl-4-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole, 2-[2'-hydroxy-3'-(1,1,3,3-tetramethylbutyl)-5'-(α,α-dimethylbenzyl)phenyl]benzotriazole;

substituted acrylates, such as ethyl- or isooctyl-α-cyano-β,β-diphenylacrylate, 2-ethylhexyl-α-cyano-β,β-diphenylacrylate, methyl-α-methoxycarbonyl-β-phenylacrylate, methyl-α-methoxycarbonyl-β-(p-methoxyphenyl)acrylate, methyl- or butyl-α-cyano-β-methyl-β-(p-methoxyphenyl)acrylate, N-(β-methoxycarbonyl-β-cyanovinyl)-2-methylindoline, octyl-p-methoxycinnamate, isopentyl-4-methoxycinnamate, urocnanic acid or salts and/or esters thereof;

esters of 4,4-diphenylbutadien-1,1-dicarbon acids, such as bis(2-ethylhexyl)ester;

derivatives of bezoxazoles;

α-(2-oxoborn-3-ylidene)toluol-4-sulfonic acid or its salts, N,N,N-trimethyl-4-(2-oxoborn-3-ylidenmethyl)anilinium-monosulfate;

dibenzoylmethanes, such as 4-tert-butyl-4'-methoxydibenzoylmethane;

belonging to class J) of triazine derivatives, such as 2,4,6-Tris-{N-[4-(2-ethylhex-1-yl)oxycarbonylphenyl]amino}-1,3,5-triazine, 4,4'-((6-(((tert.-butyl)aminocarbonyl)phenylamino)-1,3,5-triazin-2,4-diyl)imino)bis(benzoic acid-2'-ethylhexylester); 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis-(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-Hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis-(2,4-dimethylphenyl)-1,3,5-triazine, 2-(2-hydroxy-4-tridecyloxyphenyl)-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-Hydroxy-4(2-hydroxy-3-dodecyloxypropoxy)phenyl]-4,6-bis-(2,4-dimethylphenyl)-1,3,5-triazine, 2-(2-Hydroxy-4-hexyloxyphenyl)-4,6-diphenyl-1,3,5-triazine, 2-(2-hydroxy-4-methoxyphenyl)-4,6-diphenyl-1,3,5-triazine, 2,4,6-Tris[2-hydroxy-4-(3-butoxy-2-hydroxypropoxy)phenyl]-1,3,5-triazine, 2-(2-hydroxy-phenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

The term "UV filters" is understood as meaning inorganic or organic substances which are able to absorb ultraviolet rays and give off the absorbed energy again in the form of longer-wave radiation, e.g. heat. The term "UV filter" relates to one type or a mixture of different types of said compounds.

For the use as UV filters, organic substances from the groups A) to O) and mixtures thereof as described above are preferred.

The organic UV filters may be oil-soluble or water-soluble or they may be bound to a polymer, water-soluble UV filters such as compounds of classes A) and F) being preferred.

Preferable, UV filter absorb light of wavelengths between 200 and 600 nm.

The UV filters may be UV-A, UV-B filters or broadband (UV-A and UV-B) filters.

The UV filters may also be mixtures of UV filters from groups A) to O).

According to another embodiment, benzotriazole UV filters from group A) are preferred.

The UV filters and the compositions according to the invention, respectively, are suitable for combating harmful fungi and/or bacteria. They are distinguished by an outstanding effectiveness against a broad spectrum of phytopathogenic fungi and/or bacteria, including soil-borne fungi and/or bacteria, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The UV filters and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e.g. conifers; and on the plant propagation material, such as seeds, and the crop material of these plants.

Preferably, UV filters and compositions thereof, respectively are used for controlling a multitude of fungi and/or bacteria on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes. More preferably, UV filters are used for combating a multitude of fungi and/or bacteria in cereals and beets, in particular in barley.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with UV filters and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinatetolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enyzme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The UV filters and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternate*), tomatoes (e.g. *A. solani* or *A. alternate*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and or namentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grain-staining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodio-*

*phora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, and asparagus (e.g. *P. asparagi*); *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria] nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

According to another embodiment, the UV filters are suitable for controlling, preventing or treating the plant diseases caused by phytotoxin-producing fungi and/or bacteria, more preferably these plant diseases are caused by harmful fungi and/or bacteria producing photodynamically active phytotoxins.

The term "photodynamically active phytotoxins" is to be understood to denote all-fungal or bacterial toxins that require light and/or oxygen in order to exert their phytotoxic activities. Many of these "photodynamically active phytotoxins induce the production of reactive oxygen species, such as singlet oxygen, superoxide after illumination, some of which interfering in plant metabolic pathways such as photosynthetic electron transport.

According to another embodiment, the UV filters are suitable for controlling, preventing or treating the plant diseases caused by species from the genera *Ramularia*, *Cercospora*, *Dothistroma*, *Mycosphaerella*, *Fusarium*, *Alternaria*, *Aspergillus*, *Penicillium*, *Sclerotinia*, *Septoria* and/or *Pseudomonas*; particularly *Ramularia collo-cygni*.

The UV filters are particularly suitable to reduce the development of disease symptoms caused by harmful fungi and bacteria as defined above.

In another embodiment of the invention, the UV filters are suitable to reduce light-dependent disease symptoms, such as wilting, general growth suppression, chloroses, necroses, and spotting of the areal parts, caused by harmful fungi and bacteria. More preferably, the UV filters are suitable to reduce the development of light-dependent necroses and leaf spots.

More specifically, the UV filters reduce the light-dependent plant damage caused by photodynamically active phytotoxins such as rubellins, uredorubellins, caeruleoramularin, cercosporin, dothistromin, naphthazarin toxins (e.g. dihydrofusarubin, isomarticin), tentoxins, tabtoxins and cebetins.

In particular, UV filters reduce light-dependent symptom development caused by fungal and/or bacterial species from the genera *Ramularia*, *Cercospora*, *Dothistroma*, *Mycosphaerella*, *Fusarium*, *Alternaria*, *Aspergillus*, *Penicillium*, *Sclerotinia*, *Septoria* and/or *Pseudomonas*, in particular *Ramularia collo-cygni*.

In addition, the present invention provides a method of combating harmful fungi and/or bacteria in a crop plant where the method comprises, identifying a crop plant in need of disease control, and contacting the plant with an effective amount of a composition comprising a UV filter, whereby the disease of the crop plant by harmful fungi and/or bacteria is controlled. In particular, the crop plant is barley and the harmful fungus is *Ramularia collo-cygni*.

In addition, the present invention provides a method of reducing light-dependent disease symptoms, such as wilting, general growth suppression, chloroses, necroses, and spotting of the areal parts, caused by harmful fungi and/or bacteria in a crop plant, where the method comprises, identifying a crop plant in need of disease control, and contacting the plant with an effective amount of a composition comprising a UV filter, whereby the disease symptoms of the crop plant by harmful fungi and/or bacteria are controlled.

The UV filters and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae.*

The UV filters are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with UV filters as such or a composition comprising at least one UV filter prophylactically either at or before planting or transplanting.

The invention also relates to agrochemical compositions comprising a solvent or solid carrier and at least one UV filter and to the use for controlling harmful fungi.

An agrochemical composition comprises a fungicidally effective amount of a UV filter. The term "effective amount" denotes an amount of the composition or of the UV filters, which is sufficient for controlling harmful fungi or reducing or preventing the symptom development on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific UV filter used.

The UV filters can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e.g. SC, OD, FS, EC, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

Preferably, UV filters may be converted into emulsifiable concentrate type of compositions.

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wetters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalenesulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon®SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the UV filters and, if appropriate, further active substances, with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types are:

1. Composition Types for Dilution with Water i) Water-Soluble Concentrates (SL, LS)

10 parts by weight of a UV filter according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.

ii) Dispersible Concentrates (DC)

20 parts by weight of a UV filter according to the invention are dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable Concentrates (EC)

15 parts by weight of a UV filter according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of a UV filter according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of a UV filter according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of a UV filter according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of a UV filter according to the invention are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of a UV filter according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted ix) Dustable Powders (DP, DS)

5 parts by weight of a UV filter according to the invention are ground finely and mixed intimately with 95 parts by weight of finely divided kaolin. This gives a dustable composition having an active substance content of 5% by weight.

x) Granules (GR, FG, GG, MG)

0.5 parts by weight of a UV filter according to the invention is ground finely and associated with 99.5 parts by weight of carriers. Current methods are extrusion, spray-drying or the fluidized bed. This gives granules to be applied undiluted having an active substance content of 0.5% by weight.

xi) ULV Solutions (UL)

10 parts by weight of a UV filter according to the invention are dissolved in 90 parts by weight of an organic solvent, e.g. xylene. This gives a composition to be applied undiluted having an active substance content of 10% by weight.

The agrochemical compositions generally comprise between 0.01 and 95%, preferably between 0.1 and 90%, most preferably between 10 and 80%, by weight of active substance (UV filter). The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts of UV filters applied are, depending on the kind of effect desired, from 0.001 to 2 kg per ha, preferably from 0.005 to 2 kg per ha, more preferably from 0.05 to 0.9 kg per ha, in particular from 0.25 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The compositions according to the invention can, in the use form as fungicides, also be present together with other active substances, e.g. with herbicides, insecticides, growth regulators, fungicides or else with fertilizers, as pre-mix or, if appropriate, not until immediately prior to use (tank mix).

Mixing the UV filters or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The present invention also provides a method to reduce fungal resistance to a fungicide by providing an admixture of a UV filter and a fungicide compound, and treating a crop plant that is susceptible to a fungal pathogen, wherein the compounds have different modes of action to prevent or reduce fungal disease.

It is a further object of the present invention to provide, with a view to effective resistance management and effective control of harmful fungi and/or bacteria, at application rates which are as low as possible, treatments with compositions which, at a reduced total amount of active compounds applied, have improved activity against the harmful fungi and/or bacteria (synergistic mixtures) and a broadened activity spectrum, in particular for certain indications.

We have accordingly found that this object is achieved by agrochemical compositions comprising a compound UV filter as defined herein and a solvent or solid carrier and a further active compound II selected from groups A') to F'):

A') strobilurins
azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropanecarboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylidene-aminooxymethyl)-phenyl)-2-methoxyimino-N-methyl-acetamide;

B') carboxamides
carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3- dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide;

carboxylic morpholides: dimethomorph, flumorph, pyrimorph;

benzoic acid amides: flumetover, fluopicolide, fluopyram, zoxamide, N-(3-Ethyl-3,5,5-trimethyl-cyclohexyl)-3-formylamino-2-hydroxy-benzamide;

other carboxamides: carpropamid, dicyclomet, mandipromid, oxytetracyclin, silthiofarm and N-(6-methoxy-pyridin-3-yl)cyclopropanecarboxylic acid amide;

C') azoles triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;

imidazoles: cyazofamid, imazalil, pefurazoate, prochloraz, triflumizol;

benzimidazoles: benomyl, carbendazim, fuberidazole, thiabendazole;

others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

D') heterocyclic Compounds pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloro-nicotinamide, N-[(5-bromo-3-chloro-pyridin-2-yl)-methyl]-2,4-dichloro-nicotinamide;

pyrimidines: bupirimate, cyprodinil, diflumetorim, fenarimol, ferimzone, mepanipyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydropyrazole-1-carbothioic acid S-allyl ester;

others: acibenzolar-S-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo[1,5-a]pyrimidine and 5-ethyl-6-octyl-[1,2,4]triazolo[1,5-a]pyrimidine-7-ylamine;

E') carbamates thio- and dithiocarbamates: ferbam, mancozeb, maneb, metam, methasulphocarb, metiram, propineb, thiram, zineb, ziram;

carbamates: benthiavalicarb, diethofencarb, iprovalicarb, propamocarb, propamocarb hydrochlorid, valiphenal and N-(1-(1-(4-cyano-phenyl)ethanesulfonyl)-but-2-yl) carbamic acid-(4-fluorophenyl) ester;

F') other Active Substances guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dinobuton, dinocap, nitrthal-isopropyl, tecnazen, organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorous acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;

inorganic active substances: Bordeaux mixture, copper acetate, copper hydroxide, copper oxychloride, basic copper sulfate, sulfur;

others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethylphenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert-butyl-8-fluoro-2,3-dimethyl-quinolin-4-yl ester and methoxy-acetic acid 6-tert-butyl-8-fluoro-2,3-dimethyl-quinolin-4-yl ester; and G') inorganic substances: kaolin, such as Surround® (BASF SE).

The present invention furthermore relates to agrochemical compositions comprising a mixture of at least one UV filter (component 1) and at least one fungicide, e.g. one or more fungicide from the groups A') to G'), as described above, and if desired one suitable solvent or solid carrier. In another preferred embodiment, the agrochemical compositions comprises a mixture of at least one UV filter (component 1) and at least one fungicide (such as one, two, three, four or five) from the groups A') to G'), as described above, and if desired one suitable solvent or solid carrier. Those mixtures are of particular interest, since many of them at the same application rate show higher efficiencies against harmful fungi. Furthermore, combating harmful fungi with a mixture of UV filters and at least one active substance from groups A') to G'), as described above, is more efficient than combating those fungi with individual UV filters or individual active substances from groups A') to G'). By applying UV filters together with at least one active substance from groups A') to G') a synergistic effect can be obtained, i.e. more then simple addition of the individual effects is obtained (synergistic mixtures).

In the compositions comprising a UV filter and a further active compound II, the UV filter/compound II ratio is advantageously chosen so as to produce a synergistic effect.

The term "synergstic effect" is understood to refer in particular to that defined by Colby's formula (Colby, S. R., "Calculating synergistic and antagonistic responses of herbicide combinations", Weeds, 15, pp. 20-22, 1967).

The term "synergistic effect" is also understood to refer to that defined by application of the Tammes method, (Tammes, P. M. L., "Isoboles, a graphic representation of synergism in pesticides", Netherl. J. Plant Pathol. 70, 1964).

According to this invention, applying the UV filters together with at least one further active substance is to be understood to denote, that at least one UV filter and at least one further active substance occur simultaneously at the site of action (i.e. the harmful fungi to be controlled or their habitats such as infected plants, plant propagation materials, particularly seeds, surfaces, materials or the soil as well as plants, plant propagation materials, particularly seeds, soil, surfaces, materials or rooms to be protected from fungal attack) in a fungicidally effective amount. This can be obtained by applying the UV filters and at least one further active substance simultaneously, either jointly (e.g. as tankmix) or separately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one UV filter (component 1) and one further active substance (component 2), e.g. one active substance from groups A) to G), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one UV filter (component 1) and a first further active substance (component 2) and a second further active substance (component 3), e.g. two active substances from groups A) to I), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

The components can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E.g., kits may include one or more fungicide component(s) and/or an adjuvant component and/or a insecticide component and/or a growth regulator component and/or a herbicide. One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i.e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

According to one embodiment, individual components of the composition according to the invention such as parts of a kit or parts of a binary or ternary mixture may be mixed by the user himself in a spray tank and further auxiliaries may be added, if appropriate (tank mix).

In a further embodiment, either individual components of the composition according to the invention or partially premixed components, e.g. components comprising UV filters and/or active substances from the groups A') to G'), may be mixed by the user in a spray tank and further auxiliaries and additives may be added, if appropriate (tank mix).

In a further embodiment, either individual components of the composition according to the invention or partially premixed components, e.g. components comprising UV filters and/or active substances from the groups A') to G'), can be applied jointly (e.g. after tankmix) or consecutively.

Preference is also given to mixtures comprising a UV filter (component 1) and at least one active substance selected from the strobilurines of group A') (component 2) and particularly selected from azoxystrobin, dimoxystrobin, fluoxastrobin, kresoxim-methyl, orysastrobin, picoxystrobin, pyraclostrobin and trifloxystrobin.

Preference is also given to mixtures comprising a UV filter (component 1) and at least one active substance selected from the carboxamides of group B') (component 2) and particularly selected from bixafen, boscalid, sedaxane, fenhexamid, metalaxyl, isopyrazam, mefenoxam, ofurace, dimethomorph, flumorph, fluopicolid (picobenzamid), zoxamide, carpropamid, mandipropamid and N-(3',4',5'-trifluorobiphenyl-2-yl)-3-difluoromethyl-1-methyl-1H-pyrazole-4-carboxamide.

Preference is given to mixtures comprising a UV filter (component 1) and at least one active substance selected from the azoles of group C') (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

Preference is also given to mixtures comprising a UV filter (component 1) and at least one active substance selected from the heterocyclic compounds of group D') (component 2) and particularly selected from fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil, quinoxyfen and 5-ethyl-6-octyl-[1,2,4]triazolo[1,5-a]pyrimidine-7-ylamine.

Preference is also given to mixtures comprising a UV filter (component 1) and at least one active substance selected from the carbamates of group E') (component 2) and particularly selected from mancozeb, metiram, propineb, thiram, iprovalicarb, benthiavalicarb and propamocarb.

Preference is also given to mixtures comprising a UV filter (component 1) and at least one active substance selected from the fungicides given in group F') (component 2) and particularly selected from dithianon, fentin salts, such as fentin acetate, fosetyl, fosetyl-aluminium, $H_3PO_3$ and salts thereof, chlorthalonil, dichlofluanid, thiophanatmethyl, copper acetate, copper hydroxide, copper oxychloride, copper sulfate, sulfur, cymoxanil, metrafenone and spiroxamine.

Preference is also given to mixtures comprising a UV filter (component 1) and at least one active substance selected from the anorganic compounds of group G'), preferably kaolin, more preferably Surround®.

Accordingly, the present invention furthermore relates to compositions comprising one UV filter (component 1) and one further active substance (component 2), which further active substance is selected from the column "Component 2" of the lines B-1 to B-246 of Table B.

A further embodiment relates to the compositions B-1 to B-246 listed in Table B, where a row of Table B corresponds in each case to a fungicidal composition comprising one of the in the present specification individualized UV filters (component 1) and the respective further active substance from groups A') to F') (component 2) stated in the row in question. Preferably, the compositions described comprise the active substances in synergistically effective amounts.

TABLE B

Composition comprising one UV filter and one further active substance from groups A') to F')

| Mixture | Component 1 | Component 2 |
| --- | --- | --- |
| B-1 | one UV filter as defined herein | Azoxystrobin |
| B-2 | one UV filter as defined herein | Dimoxystrobin |
| B-3 | one UV filter as defined herein | Enestroburin |
| B-4 | one UV filter as defined herein | Fluoxastrobin |
| B-5 | one UV filter as defined herein | Kresoxim-methyl |
| B-6 | one UV filter as defined herein | Metominostrobin |
| B-7 | one UV filter as defined herein | Orysastrobin |
| B-8 | one UV filter as defined herein | Picoxystrobin |
| B-9 | one UV filter as defined herein | Pyraclostrobin |
| B-10 | one UV filter as defined herein | Pyribencarb |
| B-11 | one UV filter as defined herein | Trifloxystrobin |
| B-12 | one UV filter as defined herein | 2-(2-(6-(3-Chloro-2-methyl-phenoxy)-5-fluoro-pyrimidin-4-yloxy)-phenyl)-2-methoxyimino-N-methyl-acetamide |
| B-13 | one UV filter as defined herein | 2-(ortho-((2,5-Dimethylphenyl-oxymethylen)phenyl)-3-methoxy-acrylsäuremethylester |
| B-14 | one UV filter as defined herein | 3-Methoxy-2-(2-(N-(4-methoxy-phenyl)-cyclopropanecarboximidoylsulfanyl-methyl)-phenyl)-acrylic acid methyl ester |
| B-15 | one UV filter as defined herein | 2-(2-(3-(2,6-dichlorophenyl)-1-methyl-allylideneaminooxymethyl)-phenyl)-2-methoxyimino-N-methyl-acetamide |
| B-16 | one UV filter as defined herein | Benalaxyl |
| B-17 | one UV filter as defined herein | Benalaxyl-M |
| B-18 | one UV filter as defined herein | Benodanil |
| B-19 | one UV filter as defined herein | Bixafen |
| B-20 | one UV filter as defined herein | Boscalid |
| B-21 | one UV filter as defined herein | Carboxin |
| B-22 | one UV filter as defined herein | Fenfuram |
| B-23 | one UV filter as defined herein | Fenhexamid |
| B-24 | one UV filter as defined herein | Flutolanil |
| B-25 | one UV filter as defined herein | Furametpyr |
| B-26 | one UV filter as defined herein | Isopyrazam |
| B-27 | one UV filter as defined herein | Isotianil |
| B-28 | one UV filter as defined herein | Kiralaxyl |
| B-29 | one UV filter as defined herein | Mepronil |
| B-30 | one UV filter as defined herein | Metalaxyl |
| B-31 | one UV filter as defined herein | Metalaxyl-M |
| B-32 | one UV filter as defined herein | Ofurace |
| B-33 | one UV filter as defined herein | Oxadixyl |
| B-34 | one UV filter as defined herein | Oxycarboxin |
| B-35 | one UV filter as defined herein | Penthiopyrad |
| B-36 | one UV filter as defined herein | Sedaxane |
| B-37 | one UV filter as defined herein | Tecloftalam |
| B-38 | one UV filter as defined herein | Thifluzamide |
| B-39 | one UV filter as defined herein | Tiadinil |
| B-40 | one UV filter as defined herein | 2-Amino-4-methyl-thiazole-5-carboxylic acid anilide |

TABLE B-continued

Composition comprising one UV filter and one further active substance from groups A') to F')

| Mixture | Component 1 | Component 2 |
|---|---|---|
| B-41 | one UV filter as defined herein | 2-Chloro-N-(1,1,3-trimethyl-indan-4-yl)-nicotinamide |
| B-42 | one UV filter as defined herein | N-(3',4',5'-trifluorobiphenyl-2-yl)-3-difluoromethyl-1-methyl-1H-pyrazole-4-carboxamide |
| B-43 | one UV filter as defined herein | N-(4'-trifluoromethylthiobiphenyl-2-yl)-3-difluoromethyl-1-methyl-1H-pyrazole-4-carboxamide |
| B-44 | one UV filter as defined herein | N-(2-(1,3-dimethyl-butyl)-phenyl)-1,3-dimethyl-5-fluoro-1H-pyrazole-4-carboxamide |
| B-45 | one UV filter as defined herein | N-(2-(1,3,3-trimethyl-butyl)-phenyl)-1,3-dimethyl-5-fluoro-1H-pyrazole-4-carboxamide |
| B-46 | one UV filter as defined herein | Dimethomorph |
| B-47 | one UV filter as defined herein | Flumorph |
| B-48 | one UV filter as defined herein | Pyrimorph |
| B-49 | one UV filter as defined herein | Flumetover |
| B-50 | one UV filter as defined herein | Fluopicolide |
| B-51 | one UV filter as defined herein | Fluopyram |
| B-52 | one UV filter as defined herein | Zoxamide |
| B-53 | one UV filter as defined herein | N-(3-Ethyl-3,5,5-trimethyl-cyclohexyl)-3-formylamino-2-hydroxy-benzamide |
| B-54 | one UV filter as defined herein | Carpropamid |
| B-55 | one UV filter as defined herein | Diclocymet |
| B-56 | one UV filter as defined herein | Mandipropamid |
| B-57 | one UV filter as defined herein | Oxytetracyclin |
| B-58 | one UV filter as defined herein | Silthiofam |
| B-59 | one UV filter as defined herein | N-(6-methoxy-pyridin-3-yl) cyclopropanecarboxylic acid amide |
| B-60 | one UV filter as defined herein | Azaconazole |
| B-61 | one UV filter as defined herein | Bitertanol |
| B-62 | one UV filter as defined herein | Bromuconazole |
| B-63 | one UV filter as defined herein | Cyproconazole |
| B-64 | one UV filter as defined herein | Difenoconazole |
| B-65 | one UV filter as defined herein | Diniconazole |
| B-66 | one UV filter as defined herein | Diniconazole-M |
| B-67 | one UV filter as defined herein | Epoxiconazole |
| B-68 | one UV filter as defined herein | Fenbuconazole |
| B-69 | one UV filter as defined herein | Fluquinconazole |
| B-70 | one UV filter as defined herein | Flusilazole |
| B-71 | one UV filter as defined herein | Flutriafol |
| B-72 | one UV filter as defined herein | Hexaconazol |
| B-73 | one UV filter as defined herein | Imibenconazole |
| B-74 | one UV filter as defined herein | Ipconazole |
| B-75 | one UV filter as defined herein | Metconazole |
| B-76 | one UV filter as defined herein | Myclobutanil |
| B-77 | one UV filter as defined herein | Oxpoconazol |
| B-78 | one UV filter as defined herein | Paclobutrazol |
| B-79 | one UV filter as defined herein | Penconazole |
| B-80 | one UV filter as defined herein | Propiconazole |
| B-81 | one UV filter as defined herein | Prothioconazole |
| B-82 | one UV filter as defined herein | Simeconazole |
| B-83 | one UV filter as defined herein | Tebuconazole |
| B-84 | one UV filter as defined herein | Tetraconazole |
| B-85 | one UV filter as defined herein | Triadimefon |
| B-86 | one UV filter as defined herein | Triadimenol |
| B-87 | one UV filter as defined herein | Triticonazole |
| B-88 | one UV filter as defined herein | Uniconazole |
| B-89 | one UV filter as defined herein | 1-(4-Chloro-phenyl)-2-([1,2,4]triazol-1-yl)-cycloheptanol |
| B-90 | one UV filter as defined herein | Cyazofamid |
| B-91 | one UV filter as defined herein | Imazalil |
| B-92 | one UV filter as defined herein | Imazalil-sulfate |
| B-93 | one UV filter as defined herein | Pefurazoate |
| B-94 | one UV filter as defined herein | Prochloraz |
| B-95 | one UV filter as defined herein | Triflumizole |
| B-96 | one UV filter as defined herein | Benomyl |
| B-97 | one UV filter as defined herein | Carbendazim |
| B-98 | one UV filter as defined herein | Fuberidazole |
| B-99 | one UV filter as defined herein | Thiabendazole |
| B-100 | one UV filter as defined herein | Ethaboxam |
| B-101 | one UV filter as defined herein | Etridiazole |
| B-102 | one UV filter as defined herein | Hymexazole |

TABLE B-continued

Composition comprising one UV filter and one further active substance from groups A') to F')

| Mixture | Component 1 | Component 2 |
|---|---|---|
| B-103 | one UV filter as defined herein | 2-(4-Chloro-phenyl)-N-[4-(3,4-dimethoxy-phenyl)-isoxazol-5-yl]-2-prop-2-ynyloxy-acetamide |
| B-104 | one UV filter as defined herein | Fluazinam |
| B-105 | one UV filter as defined herein | Pyrifenox |
| B-106 | one UV filter as defined herein | 3-[5-(4-Chloro-phenyl)-2,3-dimethyl-isoxazolidin-3-yl]-pyridine |
| B-107 | one UV filter as defined herein | 3-[5-(4-Methyl-phenyl)-2,3-dimethyl-isoxazolidin-3-yl]-pyridine |
| B-108 | one UV filter as defined herein | 2,3,5,6-Tetrachloro-4-methanesulfonyl-pyridine |
| B-109 | one UV filter as defined herein | 3,4,5-Trichloro-pyridine-2,6-dicarbonitrile |
| B-110 | one UV filter as defined herein | N-(1-(5-Bromo-3-chloro-pyridin-2-yl)-ethyl)-2,4-dichloro-nicotinamide |
| B-111 | one UV filter as defined herein | N-((5-Bromo-3-chloro-pyridin-2-yl)-methyl)-2,4-dichloro-nicotinamide |
| B-112 | one UV filter as defined herein | Bupirimate |
| B-113 | one UV filter as defined herein | Cyprodinil |
| B-114 | one UV filter as defined herein | Diflumetorim |
| B-115 | one UV filter as defined herein | Fenarimol |
| B-116 | one UV filter as defined herein | Ferimzone |
| B-117 | one UV filter as defined herein | Mepanipyrim |
| B-118 | one UV filter as defined herein | Nitrapyrin |
| B-119 | one UV filter as defined herein | Nuarimol |
| B-120 | one UV filter as defined herein | Pyrimethanil |
| B-121 | one UV filter as defined herein | Triforine |
| B-122 | one UV filter as defined herein | Fenpiclonil |
| B-123 | one UV filter as defined herein | Fludioxonil |
| B-124 | one UV filter as defined herein | Aldimorph |
| B-125 | one UV filter as defined herein | Dodemorph |
| B-126 | one UV filter as defined herein | Dodemorph-acetate |
| B-127 | one UV filter as defined herein | Fenpropimorph |
| B-128 | one UV filter as defined herein | Tridemorph |
| B-129 | one UV filter as defined herein | Fenpropidin |
| B-130 | one UV filter as defined herein | Fluoroimid |
| B-131 | one UV filter as defined herein | Iprodione |
| B-132 | one UV filter as defined herein | Procymidone |
| B-133 | one UV filter as defined herein | Vinclozolin |
| B-134 | one UV filter as defined herein | Famoxadone |
| B-135 | one UV filter as defined herein | Fenamidone |
| B-136 | one UV filter as defined herein | Flutianil |
| B-137 | one UV filter as defined herein | Octhilinone |
| B-138 | one UV filter as defined herein | Probenazole |
| B-139 | one UV filter as defined herein | 5-Amino-2-iso-propyl-4-ortho-tolyl-2,3-dihydro-pyrazole-1-carbothioic acid S-allyl ester |
| B-140 | one UV filter as defined herein | Acibenzolar-S-methyl |
| B-141 | one UV filter as defined herein | Amisulbrom |
| B-142 | one UV filter as defined herein | Anilazin |
| B-143 | one UV filter as defined herein | Blasticidin-S |
| B-144 | one UV filter as defined herein | Captafol |
| B-145 | one UV filter as defined herein | Captan |
| B-146 | one UV filter as defined herein | Chinomethionat |
| B-147 | one UV filter as defined herein | Dazomet |
| B-148 | one UV filter as defined herein | Debacarb |
| B-149 | one UV filter as defined herein | Diclomezine |
| B-150 | one UV filter as defined herein | Difenzoquat, |
| B-151 | one UV filter as defined herein | Difenzoquat-methylsulfate |
| B-152 | one UV filter as defined herein | Fenoxanil |
| B-153 | one UV filter as defined herein | Folpet |
| B-154 | one UV filter as defined herein | Oxolinsäure |
| B-155 | one UV filter as defined herein | Piperalin |
| B-156 | one UV filter as defined herein | Proquinazid |
| B-157 | one UV filter as defined herein | Pyroquilon |
| B-158 | one UV filter as defined herein | Quinoxyfen |
| B-159 | one UV filter as defined herein | Triazoxid |
| B-160 | one UV filter as defined herein | Tricyclazole |
| B-161 | one UV filter as defined herein | 2-Butoxy-6-iodo-3-propyl-chromen-4-one |
| B-162 | one UV filter as defined herein | 5-Chloro-1-(4,6-dimethoxy-pyrimidin-2-yl)-2-methyl-1H-benzoimidazole |
| B-163 | one UV filter as defined herein | 5-Chloro-7-(4-methyl-piperidin-1-yl)-6-(2,4,6-trifluoro-phenyl)-[1,2,4]triazolo[1,5-a]pyrimidine |

TABLE B-continued

Composition comprising one UV filter and one further active substance from groups A') to F')

| Mixture | Component 1 | Component 2 |
|---|---|---|
| B-164 | one UV filter as defined herein | 5-ethyl-6-octyl-[1,2,4]triazolo[1,5-a]pyrimidine-7-ylamine |
| B-165 | one UV filter as defined herein | Ferbam |
| B-166 | one UV filter as defined herein | Mancozeb |
| B-167 | one UV filter as defined herein | Maneb |
| B-168 | one UV filter as defined herein | Metam |
| B-169 | one UV filter as defined herein | Methasulphocarb |
| B-170 | one UV filter as defined herein | Metiram |
| B-171 | one UV filter as defined herein | Propineb |
| B-172 | one UV filter as defined herein | Thiram |
| B-173 | one UV filter as defined herein | Zineb |
| B-174 | one UV filter as defined herein | Ziram |
| B-175 | one UV filter as defined herein | Diethofencarb |
| B-176 | one UV filter as defined herein | Benthiavalicarb |
| B-177 | one UV filter as defined herein | Iprovalicarb |
| B-178 | one UV filter as defined herein | Propamocarb |
| B-179 | one UV filter as defined herein | Propamocarb hydrochlorid |
| B-180 | one UV filter as defined herein | Valiphenal |
| B-181 | one UV filter as defined herein | N-(1-(1-(4-cyanophenyl)ethanesulfonyl)-but-2-yl) carbamic acid-(4-fluorophenyl) ester |
| B-182 | one UV filter as defined herein | Dodine |
| B-183 | one UV filter as defined herein | Dodine free base |
| B-184 | one UV filter as defined herein | Guazatine |
| B-185 | one UV filter as defined herein | Guazatine-acetate |
| B-186 | one UV filter as defined herein | Iminoctadine |
| B-187 | one UV filter as defined herein | Iminoctadine-triacetate |
| B-188 | one UV filter as defined herein | Iminoctadine-tris(albesilate) |
| B-189 | one UV filter as defined herein | Kasugamycin |
| B-190 | one UV filter as defined herein | Kasugamycin-hydrochloride-hydrate |
| B-191 | one UV filter as defined herein | Polyoxine |
| B-192 | one UV filter as defined herein | Streptomycin |
| B-193 | one UV filter as defined herein | Validamycin A |
| B-194 | one UV filter as defined herein | Binapacryl |
| B-195 | one UV filter as defined herein | Dicloran |
| B-196 | one UV filter as defined herein | Dinobuton |
| B-197 | one UV filter as defined herein | Dinocap |
| B-198 | one UV filter as defined herein | Nitrothal-isopropyl |
| B-199 | one UV filter as defined herein | Tecnazen |
| B-200 | one UV filter as defined herein | Fentin salts |
| B-201 | one UV filter as defined herein | Dithianon |
| B-202 | one UV filter as defined herein | Isoprothiolane |
| B-203 | one UV filter as defined herein | Edifenphos |
| B-204 | one UV filter as defined herein | Fosetyl, Fosetyl-aluminium |
| B-205 | one UV filter as defined herein | Iprobenfos |
| B-206 | one UV filter as defined herein | Phosphorous acid ($H_3PO_3$) and derivatives |
| B-207 | one UV filter as defined herein | Pyrazophos |
| B-208 | one UV filter as defined herein | Tolclofos-methyl |
| B-209 | one UV filter as defined herein | Chlorothalonil |
| B-210 | one UV filter as defined herein | Dichlofluanid |
| B-211 | one UV filter as defined herein | Dichlorophen |
| B-212 | one UV filter as defined herein | Flusulfamide |
| B-213 | one UV filter as defined herein | Hexachlorbenzene |
| B-214 | one UV filter as defined herein | Pencycuron |
| B-215 | one UV filter as defined herein | Pentachlorophenol and salts |
| B-216 | one UV filter as defined herein | Phthalide |
| B-217 | one UV filter as defined herein | Quintozene |
| B-218 | one UV filter as defined herein | Thiophanate Methyl |
| B-219 | one UV filter as defined herein | Tolylfluanid |
| B-220 | one UV filter as defined herein | N-(4-chloro-2-nitro-phenyl)-N-ethyl-4-methyl-benzenesulfonamide |
| B-221 | one UV filter as defined herein | Bordeaux mixture |
| B-222 | one UV filter as defined herein | Copper acetate |
| B-223 | one UV filter as defined herein | Copper hydroxide |
| B-224 | one UV filter as defined herein | Copper oxychloride |
| B-225 | one UV filter as defined herein | basic Copper sulfate |
| B-226 | one UV filter as defined herein | Sulfur |
| B-227 | one UV filter as defined herein | Biphenyl |
| B-228 | one UV filter as defined herein | Bronopol |
| B-229 | one UV filter as defined herein | Cyflufenamid |
| B-230 | one UV filter as defined herein | Cymoxanil |
| B-231 | one UV filter as defined herein | Diphenylamin |
| B-232 | one UV filter as defined herein | Metrafenone |
| B-233 | one UV filter as defined herein | Mildiomycin |

TABLE B-continued

Composition comprising one UV filter and one further active substance from groups A') to F')

| Mixture | Component 1 | Component 2 |
|---|---|---|
| B-234 | one UV filter as defined herein | Oxin-copper |
| B-235 | one UV filter as defined herein | Prohexadione calcium |
| B-236 | one UV filter as defined herein | Spiroxamine |
| B-237 | one UV filter as defined herein | Tolylfluanid |
| B-238 | one UV filter as defined herein | N-(Cyclopropylmethoxyimino-(6-difluoromethoxy-2,3-difluoro-phenyl)-methyl)-2-phenyl acetamide |
| B-239 | one UV filter as defined herein | N'-(4-(4-chloro-3-trifluoromethyl-phenoxy)-2,5-dimethyl-phenyl)-N-ethyl-N-methyl formamidine |
| B-240 | one UV filter as defined herein | N'-(4-(4-fluoro-3-trifluoromethyl-phenoxy)-2,5-dimethyl-phenyl)-N-ethyl-N-methyl formamidine |
| B-241 | one UV filter as defined herein | N'-(2-methyl-5-trifluoromethyl-4-(3-trimethylsilanyl-propoxy)-phenyl)-N-ethyl-N-methyl formamidine |
| B-242 | one UV filter as defined herein | N'-(5-difluoromethyl-2-methyl-4-(3-trimethylsilanyl-propoxy)-phenyl)-N-ethyl-N-methyl formamidine |
| B-243 | one UV filter as defined herein | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-244 | one UV filter as defined herein | 2-{1-[2-(5-Methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide |
| B-245 | one UV filter as defined herein | Acetic acid 6-tert.-butyl-8-fluoro-2,3-dimethyl-quinolin-4-yl ester |
| B-246 | one UV filter as defined herein | Methoxy-acetic acid 6-tert-butyl-8-fluoro-2,3-dimethyl-quinolin-4-yl ester |

The active substances referred to as component 2, their preparation and their activity against harmful fungi is known these substances are commercially available. The compounds described by IUPAC nomenclature, their preparation and their fungicidal activity are also known (cf. Can. J. Plant Sci. 48(6),587-94,1968; EP-A 141317; EP-A 152 031; EP-A226 917; EP-A243 970; EP-A 256 503; EP-A 428 941; EP-A 532 022; EP-A 1 028 125; EP-A 1 035 122; EP-A 1 201 648; EP-A 1 122244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

The mixtures of active substances can be prepared as compositions comprising besides the active ingredients at least one inert ingredient by usual means, e.g. by the means given for the compositions of UV filters.

Concerning usual ingredients of such compositions reference is made to the explanations given for the compositions containing UV filters.

The mixtures of active substances according to the present invention are suitable as fungicides, as are the UV filters. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing UV filters, respectively.

The invention is further illustrated but not limited by the following examples.

EXAMPLES

Uvinul® 3035: Ethyl-2-cyano-3,3-diphenyl acrylate, compound of the structure (4), commercially available as Uvinul® 3035 from BASF SE.

Pluriol® A350E: Polyethylene glycol monomethylether, OH-number 160 mg KOH/g, molar weight of about 350 g/mol, commercially available as Pluriol® A350E from BASF SE.

Example 1

Synthesis of UV Filter A
(2-Cyano-3,3-diphenyl-acrylsäure-[Pluriol A350E]-ester) (3)

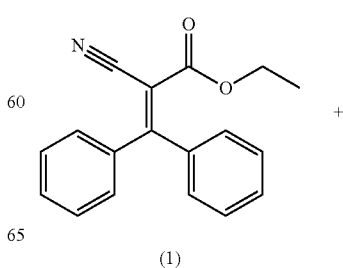

(1)

+

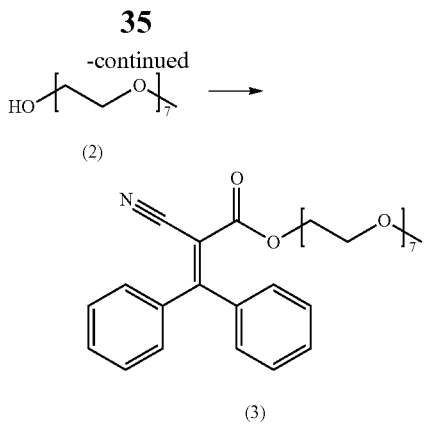

63.4 g (189 mMol) Pluriol A350E (2) were stirred for 30 min at 150° C. under nitrogen and 50.0 g (180 mMol) Uvinul 3035 (1) and 0.58 g (2 mMol) titanium(IV) isopropoxid were added. The mixture was stirred at 155° C. for 24 hours and the resulting ethanol destilled off. 200 ml methylene chloride and 350 mg (3 mMol) phosphoric acid 85% were added and the solution was left at 20° C. for 24 h. The product was purified by flash chromatography on silica. 94 g of an orange viscous liquid (3) was obtained (yield 95%).

Example 2

Preventive Action on Winter Barley Against Ramularia collo-cygni

As active substance a mixture of active substances was used called "Actives A & B", which was prepared by mixing Active A and Active B. Active A was a fungicidal suspension concentrate comprising 6 wt % epoxiconazol, 20.8 wt % boscalid, 11.2-12.6 wt % fatty alcohol alkoxylate, C8-alkyl glucoside, and phenolsulfonic acid-formaldehyde-polycondensate sodium salt (commercially available pesticide formulation from BASF SE as Champion®). Active B a fungicidal suspoemulsion comprising 20.6 wt % fenpropimorph, 11 wt % pyraclostrobin, 4.1 wt % epoxiconazol, 20.5 wt % solvent naphtha, 11 wt % fatty alcohol ethoxylate and 4.8 wt % phenolsulfonic acid-formaldehyde-polycondensate sodium salt (commercially available pesticide formulation from BASF SE as Diamant®). UV Filter A was prepared as described in example 1.

The biological trial was conducted under field conditions. The barley variety Malwinta was planted and grown under standard conditions with adequate supply of water and nutrients. At BBCH 49 an application of compounds (Table 1) was made. No other compounds were applied for pathogen control. Infection with Ramularia collo-cygni occurred naturally. The disease incidences were evaluated 12 days after application. The dosages used and the obtained results are shown in Table 1.

The diseases were converted into efficacies. An efficacy of 0 means that the infection level of the treated plants corresponds to that of the untreated control plants; an efficacy of 100 means that the treated plants were not infected. The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

TABLE 1

| Compound | Product rate (L/ha) | Dose rate (g ai/ha) | Ratio[a] | Efficacy | Expected efficacy Colby (%) |
|---|---|---|---|---|---|
| 1 Untreated control | — | — | — | 47% disease | — |
| 2 UV Filter A | 2 | 500 | — | 0 | — |
| 3 Actives A & B | 0.8 & 0.8 | 240 & 297 | — | 50 | — |
| 4 UV Filter A + Actives A & B | 2 + 0.8 & 0.8 | 500 + 240 & 297 | 2.5: 1:1 | 64 | 50 |

[a] Ratio of UV Filter: Active A:Active B

The experiments (line 2 to 4) showed that UV filters are useful for combating harmful fungi in plants compared to untreated plants (line 1). It was also demonstrated a synergistic effect of a mixture comprising an active substance and an UV filter for combating harmful fungi.

Example 3

Fungicidal Action on Various Pathogens

Various pathogens were tested under respective test mediums and concentrations of UV filters (see Table 2). The pathogens were incubated at a temperature of 18° C. for seven days. The growth of the pathogens was compared to an untreated sample. Table 2 lists the growth compared to the untreated sample, which corresponds to 100%. The growth was analyzed at 405 nm.

TABLE 2

| Pathogen | Medium | Concentration[a] | Growth[b] (%) |
|---|---|---|---|
| A: UV filter A | | | |
| 1 Phytophthora infestans | YPBG | 125 ppm | 78 |
| 2 Septoria tritici | 2% malt | 125 ppm | 40 |
| B: UV filter B | | | |
| 1 Phytophthora infestans | YPBG | 31 ppm | 77 |
| 2 Phytophthora infestans | YPBG | 125 ppm | 70 |
| 3 Septoria tritici | 2% malt | 125 ppm | 49 |
| 4 Pyricularia oryzae | 2% malt | 8 ppm | 57 |
| 5 Pyricularia oryzae | 2% malt | 31 ppm | 13 |
| 6 Pyricularia oryzae | 2% malt | 125 ppm | 0 |

[a] concentration of UV filter A in medium.
[b] Growth relative to untreated sample.

Example 4

Preventive Action on Winter Barley Against Ramularia collo-cygni

The biological trials were conducted under field conditions in Germany. The barley cultivars listed in Table 3 were planted at different locations and grown under standard conditions with adequate supply of water and nutrients. At BBCH 37-39 an application of compounds (Table 3) was made. No other compounds were applied for pathogen control. Infections with Ramularia collo-cygni occurred naturally. The disease incidences were evaluated at growth stage BBCH 75 and the degree of infection (in %) are shown in Table 3. The application rate for Active A and B was each 0.9 l/ha, for the respective UV filters 2 l/ha.

TABLE 3

| | Infection level (%) using various cultivars (brackets) at different locations A-E | | | | |
|---|---|---|---|---|---|
| Compound | A (Campanile) | B (Finita) | C (Finita) | D (Reni) | E (Fridericus) |
| 1 Untreated control | 70 | 99 | 93 | 33 | 30 |
| 2 Actives A & B | 10 | 20 | 60 | 8 | 13 |
| 3 UV Filter A + Actives A & B | 6 | 10 | 21 | 5 | 12 |
| 4 UV Filter B + Actives A & B | 8 | 15 | 28 | 5 | 11 |

The experiments (line 2 to 4) showed that UV filters, optionally in combination with active substances, are useful for combating harmful fungi in plants compared to untreated plants (line 1).

The invention claimed is:

1. A method of combating harmful fungi and/or bacteria in a crop plant where the method comprises, identifying a crop plant in need of disease control, and contacting the plant with an effective amount of a composition comprising a UV filter, whereby the disease of the crop plant by harmful fungi and/or bacteria is controlled, and wherein the UV filter is selected from the group consisting of:

A) a benzotriazole wherein said benzotriazole is 2-(2H-benzotriazol-2-yl)-4,6-bis(1-methyl-1-phenylethyl) phenol, [3-[3-(2H-benzotriazol-2-yl)-5-(1,1-dimethyl-ethyl)-4-hydroxyphenyl]-1-oxopropyl]-w-[3-[3-(2H-benzotriazol-2-yl)-5-(1,1-dimethyl-ethyl)-4-hydroxyphenyl]-1-oxopropoxy]poly(oxy-1,2-ethanediyl), 6-tert-butyl-2-(5-chloro-2H-benzotriazol-2-yl)-4-methylphenol, 2,4-di-tert-butyl-6-(5-chloro-2H-benzotriazol-2-yl)-phenol, 2-(2H-benzotriazol-2-yl)-4,6-di-tert-pentylphenol, 2-(2H-benzotriazol-2-yl)-4-(1,1,3,3-tetramethylbutyl)-phenol, 2-(2H-benzotriazol-2-yl)-4-methylphenol, 2-(2H-benzotriazol-2-yl)-4,6-bis(1-methyl-1-phenylethyl) phenol, or a compound of formula (I)

wherein
X is NH or O;
$R^1$ is $[C_2-C_4$-alkoxy$]_n$-$(C_1-C_{18}$-alkyl) or $—[CH_2CH_2NH]_n—H$;
$R^2$ is H or Cl;
$R^3$ is H or $C_1-C_8$-alkyl; and
n is an integer between 3 and 50;

B) a cyanoacrylate derivative wherein said cyanoacrylate derivative is ethyl 2-cyano-3-phenylcinnamate, 2-cyano-3,3-diphenylacrylic acid-2'-ethylhexyl ester, 2-ethylhexyl 2-cyano-3-phenylcinnamate, or a compound of formula wherein
X is NH or O;
$R^1$ is $[C_2-C_4$-alkoxy$]_n$-$(C_1-C_{18}$-alkyl) or $—[CH_2CH_2NH]_n—H$;
$R^2$ is H or Cl; and
n is an integer between 3 and 50;

C) a para-aminobenzoic acid (PABA) derivative wherein said para-aminobenzoic acid (PABA) derivative is ethyl-PABA, ethoxylated PABA, ethyl-dihydroxypropyl-PABA, Glycerol-PABA, 2-ethylhexyl 4-(dimethylamino)benzoate, 2-octyl-4-(dimethyl-amino)benzoate, amyl 4-(dimethylamino)benzoate, or 4-bis(polyethoxy)-4-amino benzoic acid polyethoxyethyl ester;

D) an ester of salicylic acid wherein said ester of salicylic acid is 2-ethylhexyl salicylate, 4-isopropylbenzyl salicylate, homomethyl salicylate, TEA salicylate, or dipropyleneglycol salicylate;

E) an ester of cinnamic acid wherein said ester of cinnamic acid is 2-ethylhexyl 4-methoxycinnamate, octyl-p-methoxycinnamate, propyl 4-methoxycinnamate, isoamyl-4-methoxycinnamate, conoxate, diisopropyl methylcinnamate, etocrylene, or a compound of formula wherein
X is NH or O;
$R^1$ is H or $[C_2-C_4$-alkoxy$]$-$(C_1-C_{18}$-alkyl) or $—[CH_2CH_2NH]_n—H$;
$R^2$ is OH or $C_1-C_8$-alkoxy;
p is an integer between 0 and 5; and
n is an integer between 3 and 50;

F) a derivative of benzophenone wherein said derivative is 2-hydroxy-4-methoxybenzophenone, 2-hydroxy-4-methoxy-4'-methylbenzophenone, 2,2'-dihydroxy-4-methoxybenzophenone, 2-(4-diethylamino-2-hydroxy-benzoyl)-benzoic acid hexylester, 4-n-octyloxy-2-hydroxy-benzophenone, a 2-hydroxybenophenone derivative selected from the group consisting of 4-hydroxy-, 4-methoxy-, 4-octyloxy-, 4-decyloxy-, 4-dodecyloxy-, 4-benzyloxy-, 4,2',4'-trihydroxy-; and 2'-hydroxy-4,4'-dimethoxy-2-hydroxybenzophenone, or a compound of formula:

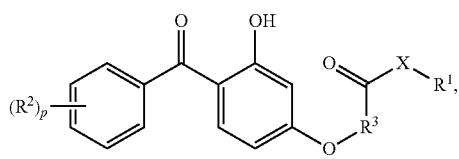

wherein
X is NH or O;
R$^1$ is H or [C$_2$-C$_4$-alkoxy]$_n$-(C$_1$-C$_{18}$-alkyl) or —[CH$_2$CH$_2$NH]$_n$—H;
R$^2$ is OH or C$_1$-C$_8$-alkoxy;
p is an integer between 0 and 5; and
R$^3$ is H or C$_1$-C$_8$-alkyl; and
n is an integer between 3 and 50;

G) a sulfonic acid derivative of benzophenones wherein said derivative is 2-hydroxy-4-methoxybenzo-phenone-5-sulfonic acid and/or its salts or 2,2'-dihydroxy-4,4'-dimethoxybenzophenone-5,5'-sulfonic acid and/or its salts;

H) a 3-benzylidenecamphor and/or a derivative thereof wherein said derivative is 3-(4'-methylbenzylidene)d-1-camphor or benzylidiene camphor sulfonic acid;

I) a sulfonic acid derivative of 3-benzylidenecamphor wherein said derivative is 4-(2-oxo-3-bornylidenemethyl)benzenesulfonic acid or 2-methyl-5-(2-oxo-3-bornyl-idene)sulfonic acid and/or salts thereof;

J) 2-ethylhexyl 4-methoxybenzmalonate;

K) a triazine derivative selected from the group consisting of dioctylbutamidotriazone, 2,4,6-trinanilino-p-(carbo-2'-ethyl-hexyl-1'-oxy)-1,3,5-triazine, 2-[4-[(2-Hydroxy-3-(2'-ethyphexyl)oxy]-2-hydroxyphenyl]-4,6bis(2,4-dimethylphenyl)-1,3,5-triazine, anisotriazine, 2,4,6-tris(diisobutyl-4'-aminobenzalmalonate)-s-triazine, and a compound of formula:

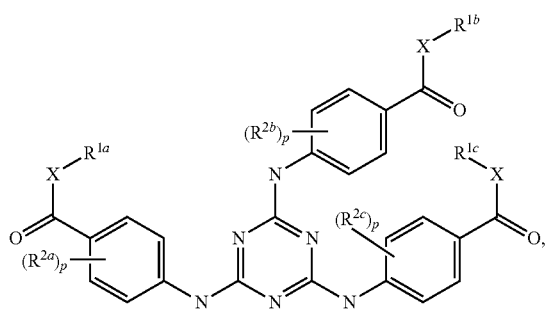

wherein
X is NH or O;
R$^{1a}$, R$^{1b}$, R$^{1c}$ are independently of each other H, [C$_2$-C$_4$-alkoxy]$_n$-(C$_1$-C$_{18}$-alkyl) or —[CH$_2$CH$_2$NH]$_n$—H;
R$^{2a}$, R$^{2b}$, R$^{2c}$ are independently of each other OH or C$_1$-C$_8$-alkoxy;
p is an integer between 0 and 4; and
n is an integer between 3 and 50;

L) 1-(4-tert-butylphenyl)-3-(4'-methoxyphenyl)propane-1,3-dione;

M) a 2-phenylbenzimidazole-5-sulfonic acid or 2-phenylbenzimidazole-4-sulfonic acid and/or their alkali metal, alkaline earth metal, ammonium, alkylammonium, alkanolammonium and/or glucammonium salt;

N) a derivative of benzoylmethaneselected from the group consisting of 1-(4'-tert-butylphenyl)-3-(4'-methoxyphenyl)propane-1,3-dione, 4-tert-butyl-4'-methoxydibenzoylmethane and 1-phenyl-3-(4'-isopropylphenyl)propane-1,3-dione;

O) an aminohydroxy-substituted derivative of benzophenones;

P) an inorganic absorber based on ZnO, TiO$_2$ or CeO$_2$; and

Q) a mixture thereof.

2. The method according to claim 1, wherein the UV filter is an organic substance selected from the groups A) to O) or a mixture of compounds from groups A) to O).

3. The method according to claim 2, wherein the UV filter is water-soluble.

4. A method of combating harmful fungi and/or bacteria in a crop plant where the method comprises, identifying a crop plant in need of disease control, and contacting the plant with an effective amount of a composition comprising a UV filter, whereby the disease of the crop plant by harmful fungi and/or bacteria is controlled, and wherein the UV filter is a benzotriazole compound.

5. The method as claimed in claim 4, where the benzotriazole compound is selected from the group consisting of 2-(2H-benzotriazol-2-yl)-4,6-bis(1-methyl-1-phenylethyl)phenol, [3-[3-(2H-benzotriazol-2-yl)-5-(1,1-dimethylethyl)-4-hydroxyphenyl]-1-oxopropyl]-w-[3-[3-(2H-benzotriazol-2-yl)-5-(1,1-dimethylethyl)-4-hydroxyphenyl]-1-oxopropoxy]poly(oxy-1,2-ethanediyl), 6-tert-butyl-2-(5-chloro-2H-benzotriazol-2-yl)-4-methylphenol, 2,4-di-tert-butyl-6-(5-chloro-2H-benzotriazol-2-yl)-phenol, 2-(2H-benzotriazol-2-yl)-4,6-di-tert-pentylphenol, 2-(2H-benzotriazol-2-yl)-4-(1,1,3,3-tetramethylbutyl)-phenol, 2-(2H-benzotriazol-2-yl)-4-methylphenol, 2-(2H-benzotriazol-2-yl)-4,6-bis(1-methyl-1-phenylethyl)phenol and a compound of formula (I),

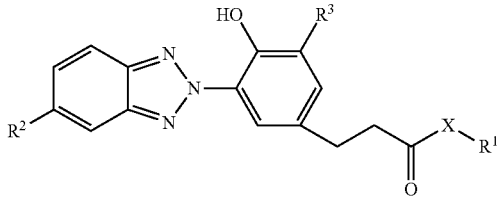

wherein
X is NH or O;
R$^1$ is [C$_2$-C$_4$-alkoxy]$_n$-(C$_1$-C$_{18}$-alkyl) or —[CH$_2$CH$_2$NH]$_n$—H;
R$^2$ is H or Cl;
R$^3$ is H or C$_1$-C$_8$-alkyl; and
n is an integer between 3 and 50.

6. The method according to claim 1, wherein wilting, general growth suppression, chloroses, necroses, or spotting of the areal parts, caused by harmful fungi and/or bacteria, is reduced.

7. The method according to claim 4, wherein wilting, general growth suppression, chloroses, necroses, and spotting of the areal parts, caused by harmful fungi and/or bacteria, is reduced.

8. The method according to claim 1, wherein the harmful fungi and/or bacteria produce photodynamically active phytotoxins.

9. The method according to claim 4, wherein the harmful fungi and/or bacteria produce photodynamically active phytotoxins.

10. The method according to claim 1, wherein the harmful fungi and/or bacteria are species from the genera *Ramularia*, Cercospora, Dothistroma, Mycosphaerella, Fusarium, Alternaria, Aspergillus, Penicillium, Sclerotinia, Septoria and/or Pseudomonas.

11. The method according to claim 4, wherein the harmful fungi and/or bacteria are species from the genera Ramularia, Cercospora, Dothistroma, Mycosphaerella, Fusarium, Alternaria, Aspergillus, Penicillium, Sclerotinia, Septoria and/or Pseudomonas.

12. The method according to claim 10, wherein the harmful fungus is Ramularia collo-cygni.

13. The method according to claim 11, wherein the harmful fungus is Ramularia collo-cygni.

14. A method of reducing a light-dependent disease symptom, where the method comprises, identifying a crop plant in need of disease control, and contacting the plant with an effective amount of a composition comprising a UV filter wherein the UV filter is selected from the group consisting of:

A) a benzotriazole wherein said benzotriazole is 2-(2H-benzotriazol-2-yl)-4,6-bis(1-methyl-1-phenylethyl) phenol, [3-[3-(2H-benzotriazol-2-yl)-5-(1,1-dimethylethyl)-4-hydroxyphenyl]-1-oxopropyl]-w-[3-[3-(2H-benzotriazol-2-yl)-5-(1,1-dimethylethyl)-4-hydroxyphenyl]-1-oxopropoxy]poly(oxy-1,2-ethanediyl), 6-tert-butyl-2-(5-chloro-2H-benzotriazol-2-yl)-4-methylphenol, 2,4-di-tert-butyl-6-(5-chloro-2H-benzotriazol-2-yl)-phenol, 2-(2H-benzotriazol-2-yl)-4,6-di-tert-pentylphenol, 2-(2H-benzotriazol-2-yl)-4-(1,1,3,3-tetramethylbutyl)-phenol, 2-(2H-benzotriazol-2-yl)-4-methylphenol, 2-(2H-benzotriazol-2-yl)-4,6-bis(1-methyl-1-phenylethyl) phenol, or a compound of formula (I)

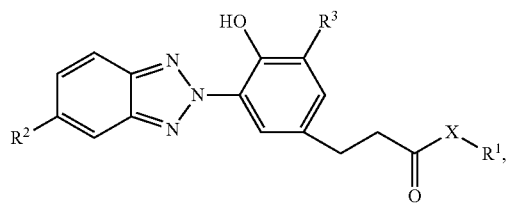

(I)

wherein
X is NH or O;
$R^1$ is $[C_2\text{-}C_4\text{-alkoxy}]_n\text{-}(C_1\text{-}C_{18}\text{-alkyl})$ or $—[CH_2CH_2NH]_n—H$;
$R^2$ is H or Cl;
$R^3$ is H or $C_1\text{-}C_8$-alkyl; and
n is an integer between 3 and 50;

B) a cyanoacrylate derivative wherein said cyanoacrylate derivative is ethyl 2-cyano-3-phenylcinnamate, 2-cyano-3,3-diphenylacrylic acid-2'-ethylhexyl ester, 2-ethylhexyl 2-cyano-3-phenylcinnamate, or a compound of formula

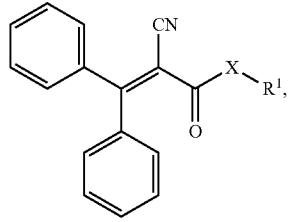

wherein
X is NH or O;
$R^1$ is $[C_2\text{-}C_4\text{-alkoxy}]_n\text{-}(C_1\text{-}C_{18}\text{-alkyl})$ or $—[CH_2CH_2NH]_n—H$;
$R^2$ is H or Cl; and
n is an integer between 3 and 50;

C) a para-aminobenzoic acid (PABA) derivative wherein said para-aminobenzoic acid (PABA) derivative is ethyl-PABA, ethoxylated PABA, ethyl-dihydroxypropyl-PABA, Glycerol-PABA, 2-ethylhexyl 4-(dimethylamino)benzoate, 2-octyl-4-(dimethyl-amino)benzoate, amyl 4-(dimethylamino)benzoate, or 4-bis(polyethoxy)-4-amino benzoic acid polyethoxyethyl ester;

D) an ester of salicylic acid wherein said ester of salicylic acid is 2-ethylhexyl salicylate, 4-isopropylbenzyl salicylate, homomethyl salicylate, TEA salicylate, or dipropyleneglycol salicylate;

E) an ester of cinnamic acid wherein said ester of cinnamic acid is 2-ethylhexyl 4-methoxycinnamate, octyl-p-methoxycinnamate, propyl 4-methoxycinnamate, isoamyl-4-methoxycinnamate, conoxate, diisopropyl methylcinnamate, etocrylene, a compound of formula

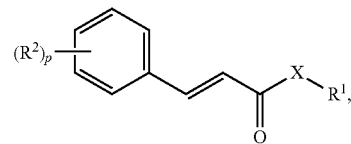

wherein
X is NH or O;
$R^1$ is H or $[C_2\text{-}C_4\text{-alkoxy}]_n\text{-}(C_1\text{-}C_{18}\text{-alkyl})$ or $—[CH_2CH_2NH]_n—H$;
$R^2$ is OH or $C_1\text{-}C_8$-alkoxy;
p is an integer between 0 and 5; and
n is an integer between 3 and 50;

F) a derivative of benzophenone wherein said derivative is 2-hydroxy-4-methoxybenzophenone, 2-hydroxy-4-methoxy-4'-methylbenzophenone, 2,2'-dihydroxy-4-methoxybenzophenone, 2-(4-diethylamino-2-hydroxy-benzoyl)-benzoic acid hexylester, 4-n-octyloxy-2-hydroxy-benzophenone, a 2-hydroxybenophenone derivative selected from the group consisting of 4-hydroxy-, 4-methoxy-, 4-octyloxy-, 4-decyloxy-, 4-dodecyloxy-, 4-benzyloxy-, 4,2',4'-trihydroxy-; and 2'-hydroxy-4,4'-dimethoxy-2-hydroxybenzophenone, or a compound of formula:

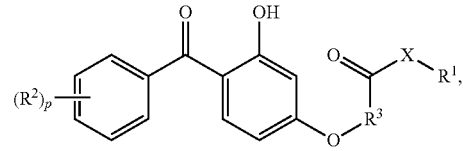

wherein
X is NH or O;
$R^1$ is H or $[C_2\text{-}C_4\text{-alkoxy}]_n\text{-}(C_1\text{-}C_{18}\text{-alkyl})$ or $—[CH_2CH_2NH]_n—H$;
$R^2$ is OH or $C_1\text{-}C_8$-alkoxy;
p is an integer between 0 and 5; and
$R^3$ is H or $C_1\text{-}C_8$-alkyl; and
n is an integer between 3 and 50;

G) a sulfonic acid derivative of benzophenones wherein said derivative is 2-hydroxy-4-methoxybenzo-phenone-5-sulfonic acid and/or its salts or 2,2'-dihydroxy-4,4'-dimethoxybenzophenone-5,5'-sulfonic acid and/or its salts;

H) a 3-benzylidenecamphor and/or a derivative thereof wherein said derivative is 3-(4'-methylbenzylidene)d-1-camphor or benzylidiene camphor sulfonic acid;

I) a sulfonic acid derivative of 3-benzylidenecamphor wherein said derivative is 4-(2-oxo-3-bornylidenemethyl)benzenesulfonic acid or 2-methyl-5-(2-oxo-3-bornyl-idene)sulfonic acid and/or salts thereof;

J) 2-ethylhexyl 4-methoxybenzmalonate;

K) a triazine derivative selected from the group consisting of dioctylbutamidotriazone, 2,4,6-trinanilino-p-(carbo-2'-ethyl-hexyl-1'-oxy)-1,3,5-triazine, 2-[4-[(2-Hydroxy-3-(2'-ethyl)hexyl)oxy]-2-hydroxyphenyl]-4,6bis (2,4-dimethylphenyl)-1,3,5-triazine, anisotriazine, 2,4, 6-tris(diisobutyl-4'-aminobenzalmalonate)-s-triazine, and a compound of formula:

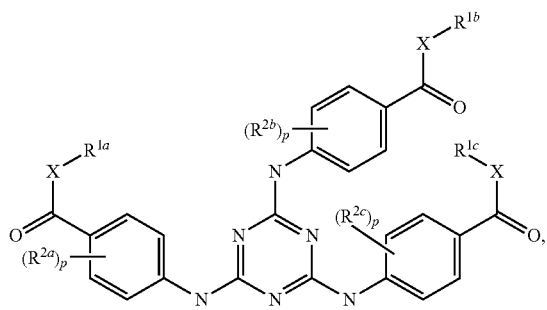

wherein
X is NH or O;
$R^{1a}, R^{1b}, R^{1c}$ are independently of each other H, $[C_2-C_4-alkoxy]_n-(C_1-C_{18}-alkyl)$ or $—[CH_2CH_2NH]_n—H$;
$R^{2a}, R^{2b}, R^{2c}$ are independently of each other OH or $C_1-C_8$alkoxy;
p is an integer between 0 and 4; and
n is an integer between 3 and 50;

L) 1-(4-tert-butylphenyl)-3-(4'-methoxyphenyl)propane-1,3-dione;

M) a 2-phenylbenzimidazole-5-sulfonic acid or 2-phenylbenzimidazole-4-sulfonic acid and/or their alkali metal, alkaline earth metal, ammonium, alkylammonium, alkanolammonium and/or glucammonium salt;

N) a derivative of benzoylmethane selected from the group consisting of 1-(4'-tcrt-butylphenyl)-3-(4'-methoxyphenyl)propane-1,3-dione, 4-tert-butyl-4'-methoxydibenzoylmethane and 1-phenyl-3-(4'-isopropylphenyl)propane-1,3-dione;

O) an aminohydroxy-substituted derivative of benzophenones;

P) an inorganic absorber based on $ZnO$, $TiO_2$ or $CeO_2$; and a mixture thereof;

whereby the disease symptom of the crop plant by harmful fungi and/or bacteria is controlled, and wherein said disease symptom is wilting, general growth suppression, chloroses, necroses, and spotting of the areal parts, caused by harmful fungi and/or bacteria in a crop plant.

15. A method of reducing a light-dependent disease symptom, wherein the method comprises, identifying a crop plant in need of disease control, and contacting the plant with an effective amount of a composition comprising a UV filter, wherein the UV filter is a benzotriazole compound, whereby the disease symptoms of the crop plant by harmful fungi and/or bacteria is controlled, and wherein the disease symptom is wilting, general growth suppression, chloroses, necroses, and spotting of the areal parts, caused by harmful fungi and/or bacteria in a crop plant.

16. The method according to claim 14, wherein the harmful fungi and/or bacteria are species from the genera *Ramularia, Cercospora, Dothistroma, Mycosphaerella, Fusarium, Alternaria, Aspergillus, Penicillium, Sclerotinia, Septoria* and/or *Pseudomonas*.

17. The method according to claim 15, wherein the harmful fungi and/or bacteria are species from the genera *Ramularia, Cercospora, Dothistroma, Mycosphaerella, Fusarium, Alternaria, Aspergillus, Penicillium, Sclerotinia, Septoria* and/or *Pseudomonas*.

18. The method according to claim 1, wherein the crop plant is a cereal plant.

19. The method according to claim 4, wherein the crop plant is a cereal plant.

20. The method according to claim 14, wherein the crop plant is a cereal plant.

21. The method according to claim 15, wherein the crop plant is a cereal plant.

22. A method according to claim 18, wherein the crop plant is barley and the harmful fungus is *Ramularia collo-cygni*.

23. The method according to claim 19, wherein the crop plant is barley and the harmful fungus is *Ramularia collo-cygni*.

24. The method according to claim 20, wherein the crop plant is barley and the harmful fungus is *Ramularia collo-cygni*.

25. The method according to claim 21, wherein the crop plant is barley and the harmful fungus is *Ramularia collo-cygni*.

26. The method according to claim 1, wherein the composition further comprises an active substance selected from the following groups:

A') a strobilurin selected from the group consisting of azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxyphenyl)-cyclopropane-carboximidoyl-sulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methylacetamide;

B') a carboxamide selected from the group consisting of carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide;

carboxylic morpholides: dimethomorph, flumorph, pyrimorph;

benzoic acid amides: flumetover, fluopicolide, fluopyram, zoxamide, N-(3-Ethyl-3,5,5-trimethyl-cyclohexyl)-3-formylamino-2-hydroxy-benzamide; and other carboxamides: carpropamid, dicyclomet, mandiproamid, oxytetracyclin, silthiofarm and N-(6-methoxy-pyridin-3-yl)cyclopropanecarboxylic acid amide;

C') an azole selected from the group consisting of triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothio-conazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;

imidazoles: cyazofamid, imazalil, pefurazoate, prochloraz, triflumizol;

benzimidazoles: benomyl, carbendazim, fuberidazole, thiabendazole; and others: ethaboxam, etridiazole, hymexazole and 2-(4-chloro-phenyl)-N-[4-(3,4-di-methoxy-phenyl)-isoxazol-5-yl]-2-prop-2-ynyloxy-acetamide;

D') a heterocyclic compound selected from the group consisting of pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloro-nicotinamide, N-[(5-bromo-3-chloro-pyridin-2-yl)-methyl]-2,4-dichloro-nicotinamide;

pyrimidines: bupirimate, cyprodinil, diflumetorim, fenarimol, ferimzone, mepani-pyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester; and others: acibenzolar-S-methyl, amisulbrom, anilazin, blasticidin-S, captafol, captan, chinomethionat, dazomet, debacarb, diclomezine, difenzoquat, difenzoquat-methyl-sulfate, fenoxanil, Folpet, oxolinic acid, piperalin, proquinazid, pyroquilon, quin-oxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo-[1,5-a]pyrimidine and 5-ethyl-6-octyl-[1,2,4]triazolo[1,5-a]pyrimidine-7-ylamine;

E') a carbamate selected from the group consisting of thio- and dithiocarbamates: ferbam, mancozeb, maneb, metam, methasulphocarb, metiram, propineb, thiram, zineb, ziram; and carbamates: benthiavalicarb, diethofencarb, iprovalicarb, propamocarb, propamo-carb hydrochlorid, valiphenal and N-(1-(1-(4-cyano-phenyl)ethanesulfonyl)-but-2-yl) carbamic acid-(4-fluorophenyl) ester;

F') another active substance selected from the group consisting of guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, poly-oxine, validamycin A;

nitrophenyl derivates: binapacryl, dinobuton, dinocap, nitrthal-isopropyl, tecnazen, organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorous acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;

inorganic active substances: Bordeaux mixture, copper acetate, copper hydroxide, copper oxychloride, basic copper sulfate, sulfur; and others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert-butyl-8-fluoro-2,3-dimethyl-quinolin-4-yl ester and methoxy-acetic acid 6-tert-butyl-8-fluoro-2,3-dimethyl-quinolin-4-yl ester; and G') kaolin.

27. The method according to claim 4, wherein the composition comprises a mixture of at least one UV filter and at least one active substance selected from the following groups:

A') a strobilurin selected from the group consisting of azoxystrobin, dimoxystrobin, enestroburin, fluoxastrobin, kresoxim-methyl, meto-minostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylidene-aminooxymethyl)-phenyl)-2-methoxyimino-N-methyl-acetamide;

B') a carboxamide selected from the group consisting of
carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide;
carboxylic morpholides: dimethomorph, flumorph, pyrimorph;
benzoic acid amides: flumetover, fluopicolide, fluopyram, zoxamide, N-(3-Ethyl-3,5,5-trimethyl-cyclohexyl)-3-formylamino-2-hydroxy-benzamide; and
other carboxamides: carpropamid, dicyclomet, mandiproamid, oxytetracyclin, silthiofarm and N-(6-methoxy-pyridin-3-yl)cyclopropanecarboxylic acid amide;

C') an azole selected from the group consisting of
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothio-conazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;
imidazoles: cyazofamid, imazalil, pefurazoate, prochloraz, triflumizol;
benzimidazoles: benomyl, carbendazim, fuberidazole, thiabendazole; and
others: ethaboxam, etridiazole, hymexazole and 2-(4-chloro-phenyl)-N-[4-(3,4-di-methoxy-phenyl)-isoxazol-5-yl]-2-prop-2-ynyloxy-acetamide;

D') a heterocyclic compound selected from the group consisting of
pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloro-nicotinamide, N-[(5-bromo-3-chloro-pyridin-2-yl)-methyl]-2,4-dichloro-nicotinamide;
pyrimidines: bupirimate, cyprodinil, diflumetorim, fenarimol, ferimzone, mepani-pyrim, nitrapyrin, nuarimol, pyrimethanil;
piperazines: triforine;
pyrroles: fenpiclonil, fludioxonil;
morpholines: aldimorph, dodemorph, dodemorph-acetate, fenpropimorph, tridemorph;
piperidines: fenpropidin;
dicarboximides: fluoroimid, iprodione, procymidone, vinclozolin;
non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester; and
others: acibenzolar-S-methyl, amisulbrom, anilazin, blasticidin-S, captafol, captan, chinomethionat, dazomet, debacarb, diclomezine, difenzoquat, difenzoquat-methyl-sulfate, fenoxanil, Folpet, oxolinic acid, piperalin, proquinazid, pyroquilon, quin-oxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo-[1,5-a]pyrimidine and 5-ethyl-6-octyl-[1,2,4]triazolo[1,5-a]pyrimidine-7-ylamine;

E') a carbamate selected from the group consisting of
thio- and dithiocarbamates: ferbam, mancozeb, maneb, metam, methasulphocarb, metiram, propineb, thiram, zineb, ziram; and
carbamates: benthiavalicarb, diethofencarb, iprovalicarb, propamocarb, propamo-carb hydrochlorid, valiphenal and N-(1-(1-(4-cyano-phenyl)ethanesulfonyl)-but-2-yl) carbamic acid-(4-fluorophenyl) ester;

F') another active substance selected from the group consisting of
guanidines: guanidine, dodine, dodine free base, guazatine, guazatine-acetate, iminoctadine, iminoctadine-triacetate, iminoctadine-tris(albesilate);
antibiotics: kasugamycin, kasugamycin hydrochloride-hydrate, streptomycin, poly-oxine, validamycin A;
nitrophenyl derivates: binapacryl, dinobuton, dinocap, nitrthal-isopropyl, tecnazen, organometal compounds: fentin salts, such as fentin-acetate, fentin chloride or fentin hydroxide;
sulfur-containing heterocyclyl compounds: dithianon, isoprothiolane;
organophosphorus compounds: edifenphos, fosetyl, fosetyl-aluminum, iprobenfos, phosphorous acid and its salts, pyrazophos, tolclofos-methyl;
organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;
inorganic active substances: Bordeaux mixture, copper acetate, copper hydroxide, copper oxychloride, basic copper sulfate, sulfur;
others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5- methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert-butyl-8-fluoro-2,3-dimethyl-quinolin-4-yl ester and methoxy-acetic acid 6-tert-butyl-8-fluoro-2,3-dimethyl-quinolin-4-yl ester; and G') kaolin.

28. The method according to claim 14, wherein the composition comprises a mixture of at least one UV filter and at least one active substance selected from the following groups:

A') a strobilurin selected from the group consisting of
azoxystrobin, dimoxystrobin, enestroburin, fluoxastrobin, kresoxim-methyl, meto-minostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylidene-aminooxymethyl)-phenyl)-2-methoxyimino-N-methyl-acetamide;

B') a carboxamide selected from the group consisting of
carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide;

carboxylic morpholides: dimethomorph, flumorph, pyrimorph;

benzoic acid amides: flumetover, fluopicolide, fluopyram, zoxamide, N-(3-Ethyl-3,5,5-trimethyl-cyclohexyl)-3-formylamino-2-hydroxy-benzamide; and other carboxamides: carpropamid, dicyclomet, mandiproamid, oxytetracyclin, silthiofarm and N-(6-methoxy-pyridin-3-yl)cyclopropanecarboxylic acid amide;

C') an azole selected from the group consisting of
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothio-conazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;

imidazoles: cyazofamid, imazalil, pefurazoate, prochloraz, triflumizol;

benzimidazoles: benomyl, carbendazim, fuberidazole, thiabendazole; and others: ethaboxam, etridiazole, hymexazole and 2-(4-chloro-phenyl)-N-[4-(3,4-di-methoxy-phenyl)-isoxazol-5-yl]-2-prop-2-ynyloxy-acetamide;

D') a heterocyclic compound selected from the group consisting of
pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloro-nicotinamide, N-[(5-bromo-3-chloro-pyridin-2-yl)-methyl]-2,4-dichloro-nicotinamide;

pyrimidines: bupirimate, cyprodinil, diflumetorim, fenarimol, ferimzone, mepani-pyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester; and others: acibenzolar-S-methyl, amisulbrom, anilazin, blasticidin-S, captafol, captan, chinomethionat, dazomet, debacarb, diclomezine, difenzoquat, difenzoquat-methyl-sulfate, fenoxanil, Folpet, oxolinic acid, piperalin, proquinazid, pyroquilon, quin-oxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]-triazolo-[1,5-a]pyrimidine and 5-ethyl-6-octyl-[1,2,4]triazolo[1,5-a]pyrimidine-7-ylamine;

E') a carbamate selected from the group consisting of
thio- and dithiocarbamates: ferbam, mancozeb, maneb, metam, methasulphocarb, metiram, propineb, thiram, zineb, ziram; and carbamates: benthiavalicarb, diethofencarb, iprovalicarb, propamocarb, propamo-carb hydrochlorid, valiphenal and N-(1-(1-(4-cyano-phenyl)ethanesulfonyl)-but-2-yl) carbamic acid-(4-fluorophenyl) ester;

F') another active substance selected from the group consisting of
guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, poly-oxine, validamycin A;

nitrophenyl derivates: binapacryl, dinobuton, dinocap, nitrthal-isopropyl, tecnazen, organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorous acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;

inorganic active substances: Bordeaux mixture, copper acetate, copper hydroxide, copper oxychloride, basic copper sulfate, sulfur;

others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert-butyl-8-fluoro-2,3-dimethyl-quinolin-4-yl ester and methoxy-acetic acid 6-tert-butyl-8-fluoro-2,3-dimethyl-quinolin-4-yl ester; and G') kaolin.

29. The method according to claim 5, wherein the composition comprises a mixture of at least one UV filter and at least one active substance selected from the following groups:

A') a strobilurin selected from the group consisting of azoxystrobin, dimoxystrobin, enestroburin, fluoxastrobin, kresoxim-methyl, meto-minostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxyphenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylidene-aminooxymethyl)-phenyl)-2-methoxyimino-N-methyl-acetamide;

B') a carboxamide selected from the group consisting of carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide;

carboxylic morpholides: dimethomorph, flumorph, pyrimorph;

benzoic acid amides: flumetover, fluopicolide, fluopyram, zoxamide, N-(3-Ethyl-3,5,5-trimethyl-cyclohexyl)-3-formylamino-2-hydroxy-benzamide; and other carboxamides: carpropamid, dicyclomet, mandiproamid, oxytetracyclin, silthiofarm and N-(6-methoxy-pyridin-3-yl)cyclopropanecarboxylic acid amide;

C') an azole selected from the group consisting of triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothio-conazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;

imidazoles: cyazofamid, imazalil, pefurazoate, prochloraz, triflumizol;

benzimidazoles: benomyl, carbendazim, fuberidazole, thiabendazole; and others: ethaboxam, etridiazole, hymexazole and 2-(4-chloro-phenyl)-N-[4-(3,4-di-methoxy-phenyl)-isoxazol-5-yl]-2-prop-2-ynyloxy-acetamide;

D') a heterocyclic compound selected from the group consisting of pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloro-nicotinamide, N-[(5-bromo-3-chloro-pyridin-2-yl)-methyl]-2,4-dichloro-nicotinamide;

pyrimidines: bupirimate, cyprodinil, diflumetorim, fenarimol, ferimzone, mepani-pyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester; and others: acibenzolar-S-methyl, amisulbrom, anilazin, blasticidin-S, captafol, captan, chinomethionat, dazomet, debacarb, diclomezine, difenzoquat, difenzoquat-methyl-sulfate, fenoxanil, Folpet, oxolinic acid, piperalin, proquinazid, pyroquilon, quin-oxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo-[1,5-a]pyrimidine and 5-ethyl-6-octyl-[1,2,4]-triazolo[1,5-a]pyrimidine-7-ylamine;

E') a carbamate selected from the group consisting of thio- and dithiocarbamates: ferbam, mancozeb, maneb, metam, methasulphocarb, metiram, propineb, thiram, zineb, ziram; and carbamates: benthiavalicarb, diethofencarb, iprovalicarb, propamocarb hydrochlorid, valiphenal and N-(1-(1-(4-cyano-phenyl)ethanesulfonyl)-but-2-yl) carbamic acid-(4-fluorophenyl) ester;

F') another active substance selected from the group consisting of
  guanidines: guanidine, dodine, dodine free base, guazatine, guazatine-acetate, iminoctadine, iminoctadine-triacetate, iminoctadine-tris(albesilate);
  antibiotics: kasugamycin, kasugamycin hydrochloride-hydrate, streptomycin, poly-oxine, validamycin A;
  nitrophenyl derivates: binapacryl, dinobuton, dinocap, nitrthal-isopropyl, tecnazen, organometal compounds: fentin salts, such as fentin-acetate, fentin chloride or fentin hydroxide;
  sulfur-containing heterocyclyl compounds: dithianon, isoprothiolane;
  organophosphorus compounds: edifenphos, fosetyl, fosetyl-aluminum, iprobenfos, phosphorous acid and its salts, pyrazophos, tolclofos-methyl;
  organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;
  inorganic active substances: Bordeaux mixture, copper acetate, copper hydroxide, copper oxychloride, basic copper sulfate, sulfur;
  others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert-butyl-8-fluoro-2,3-dimethyl-quinolin-4-yl ester and methoxy-acetic acid 6-tert-butyl-8-fluoro-2,3-dimethyl-quinolin-4-yl ester; and
G') kaolin.

* * * * *

UNITED STATES PATENT AND TRADEMARK OFFICE
CERTIFICATE OF CORRECTION

PATENT NO. : 8,748,347 B2
APPLICATION NO. : 13/260796
DATED : June 10, 2014
INVENTOR(S) : Riggs et al.

It is certified that error appears in the above-identified patent and that said Letters Patent is hereby corrected as shown below:

In the Claims

Claim 1, col. 39, lines 32-34, delete "2-[4-[(2-Hydroxy-3-(2'-ethyphexyl)oxy]-2-hydroxyphenyl]-4,6bis(2,4-dimethylphenyldimeth- ylphenyl)-1,3,5-triazine" and insert therefore --2-[4-[(2-Hydroxy-3-(2'-ethyl)hexyl)oxy]-2-hydroxyphenyl]-4,6bis(2,4-dimethylphenyldimeth- ylphenyl)-1,3,5-triazine--.

Claim 14, col. 43, lines 46-47, delete "1-(4'-tcrt-butylphenyl)-3-(4'-methoxyphenyl)propane-1,3-dione" and insert therefore --1-(4'-tert-butylphenyl)-3-(4'-methoxyphenyl)propane-1,3-dione--.

Signed and Sealed this
Thirtieth Day of June, 2015

Michelle K. Lee
*Director of the United States Patent and Trademark Office*